(12) United States Patent
Wendt et al.

(10) Patent No.: US 7,750,004 B2
(45) Date of Patent: Jul. 6, 2010

(54) APOPTOSIS PROMOTERS

(75) Inventors: Michael D. Wendt, Vernon Hills, IL (US); Hong Ding, Gurnee, IL (US); Sheela A. Thomas, Libertyville, IL (US); Steven W. Elmore, Northbrook, IL (US); Wang Shen, San Mateo, CA (US); Daniel A. Dickman, San Ramon, CA (US); David Augeri, Princeton, NJ (US)

(73) Assignee: Abbott Laboratories, Abbott Park, IL (US)

( * ) Notice: Subject to any disclaimer, the term of this patent is extended or adjusted under 35 U.S.C. 154(b) by 568 days.

(21) Appl. No.: 11/482,458

(22) Filed: Jul. 7, 2006

(65) Prior Publication Data

US 2007/0135392 A1      Jun. 14, 2007

Related U.S. Application Data

(60) Provisional application No. 60/697,123, filed on Jul. 7, 2005.

(51) Int. Cl.
*A61K 31/5375* (2006.01)
*C07D 265/30* (2006.01)

(52) U.S. Cl. .................................. 514/239.2; 544/107
(58) Field of Classification Search ............. 514/239.2; 544/107
See application file for complete search history.

(56) References Cited

U.S. PATENT DOCUMENTS

2002/0055631 A1   5/2002   Augeri et al.
2002/0086887 A1   7/2002   Augeri et al.

FOREIGN PATENT DOCUMENTS

WO           0224636        3/2002
WO          2006062093      6/2005

OTHER PUBLICATIONS

Petros Am, et al., "Discovery of a Potent Inhibitor of the Antipoptotic Protein Bcl-XL from NMR and parallel Systhesis", Journal of Medicinal Chemistry, 2006, pp. 656-663, vol. 49, American Chemical Society.

*Primary Examiner*—Taofiq A Solola
(74) *Attorney, Agent, or Firm*—Oona A. Manzari

(57) ABSTRACT

Compounds which inhibit the activity of anti-apoptotic Mcl-1 protein, compositions containing the compounds and methods of treating diseases during which are expressed the Mcl-1 protein are disclosed.

3 Claims, No Drawings

APOPTOSIS PROMOTERS

This application claims priority to U.S. provisional Application Ser. No. 60/697,123, Jul. 7, 2005.

FIELD OF THE INVENTION

This invention pertains to compounds which inhibit the activity of anti-apoptotic Mcl-1 protein, compositions containing the compounds and methods of treating diseases during which are expressed the Mcl-1 protein.

BACKGROUND OF THE INVENTION

Mcl-1 protein is associated with a number of diseases. There is therefore an existing need in the therapeutic arts for compounds which bind to and inhibit the activity of Mcl-1 protein.

SUMMARY OF THE INVENTION

One embodiment of this invention, therefore, pertains to compounds which bind to and inhibit the activity Mcl-1 protein, the compounds having formula (I),

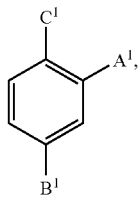

(I)

and therapeutically acceptable salts, prodrugs, salts of prodrugs and metabolites thereof, wherein $A^1$ is $A^2$, $A^3$, $A^4$ or $A^5$;

$A^2$ is $C_1$-$C_5$-alkyl, $C_2$-$C_5$-alkenyl or $C_2$-$C_5$-alkynyl, each of which is substituted with $R^1$ and further unsubstituted or substituted with one or two of independently selected OH, $O(CH_3)$, $NH_2$, $NH(CH_3)$ or $N(CH_3)_2$;

$A^3$ is $OR^1$, $NHR^1$, $N(R^4)R^1$, $SR^1$, $S(O)R^1$, $SO_2R^1$, $C(O)R^1$, $C(S)R^1$, $L^1OR^1$, $L^1NHR^1$, $L^1N(R^4)R^1$, $L^1SR^1$, $L^1S(O)R^1$, $L^1SO_2R^1$, $L^1C(O)R^1$, $L^1C(S)R^1$, $OL^1R^1$, $NHL^1R^1$, $N(R^4)L^1R^1$, $SL^1R^1$, $S(O)L^1R^1$, $SO_2L^1R^1$, $C(O)L^1R^1$ or $C(S)L^1R^1$, wherein $L^1$ $C_1$-$C_4$-alkylene or $C_3$-$C_4$-alkenylene and $R^4$ is alkyl;

$A^4$ is $OC(O)R^1$, $C(O)OR^1$, $SC(O)R^1$, $C(S)OR^1$, $NHC(O)R^1$, $C(O)NHR^1$, $NHSO_2R^1$, $SO_2NHR^1$, $N(R^4)C(O)R^1$, $C(O)N(R^4)R^1$, $N(R^4)SO_2R^1$, $SO_2N(R^4)R^1$, $L^2OC(O)R^1$, $L^2C(O)OR^1$, $L^2SC(O)R^1$, $L^2C(S)OR^1$, $L^2NHC(O)R^1$, $L^2C(O)NHR^1$, $L^2NHSO_2R^1$, $L^2SO_2NHR^1$, $L^2N(R^4)C(O)R^1$, $L^2C(O)N(R^4)R^1$, $L^2N(R^4)SO_2R^1$, $L^2SO_2N(R^4)R^1$, $OC(O)L^2R^1$, $C(O)OL^2R^1$, $SC(O)L^2R^1$, $C(S)OL^2R^1$, $NHC(O)L^2R^1$, $C(O)NHL^2R^1$, $NHSO_2L^2R^1$, $SO_2NHL^2R^1$, $N(R^4)C(O)L^2R^1$, $C(O)N(R^4)L^2R^1$, $N(R^4)SO_2L^2R^1$, $SO_2N(R^4)L^2R^1$, wherein $L^2$ is $C_1$-$C_3$-alkylene or $C_2$-$C_3$-alkenylene;

$A^5$ is $NHC(O)NHR^1$, $NHSO_2NHR^1$, $N(R^4)C(O)N(R^4)R^1$, $N(R^4)SO_2N(R^4)R^1$, $L^3NHC(O)NHR^1$, $L^3NHSO_2NHR^1$, $L^3N(R^4)C(O)N(R^4)R^1$, $L^3N(R^4)SO_2N(R^4)R^1$, $NHC(O)NHL^3R^1$, $NHSO_2NHL^3R^1$, $N(R^4)C(O)N(R^4)L^3R^1$, $N(R^4)SO_2N(R^4)L^3R^1$, wherein $L^3$ is $C_1$-$C_2$-alkylene;

$R^1$ is $R^2$, $OR^2$, $NHR^2$, $N(R^2)_2$, $SR^2$, $S(O)R^2$, $SO_2R^2$, $NHSO_2R^2$, $SO_2NHR^2$, $R^3$, $OR^3$, $NHR^3N(R^2)_2$, $SR^3$, $S(O)R^3$, $SO_2R^3$, $NHSO_2R^3$, $SO_2NHR^3$, $R^4$, $OR^4$, $NHR^4$, $N(R^4)_2$, $SO_2NHR^4$, $SR^4$, $S(O)R^4$, $SO_2R^4NHSO_2R^4$ or $SO_2NHR^4$;

$R^2$ is phenyl which is unfused or fused with benzene, heteroarene or $R^{2A}$, wherein $R^{2A}$ is cycloalkane, cycloalkene, heterocycloalkane or heterocycloalkene;

$R^3$ is heteroaryl which is unfused or fused with benzene, heteroarene or $R^{3A}$, wherein $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$, wherein $R^{4A}$ is cycloalkane, cycloalkene, heterocycloalkane or heterocycloalkene;

$B^1$ is phenyl substituted with one or two of independently selected F, Br, Cl or I;

$C^1$ is $C^2$ or $C^3$;

$C^2$ is CN, $NO_2$, C(O)OH, F, Cl, Br, I, $CF_3$, $OCF_3$, $CF_2CF_3$, $OCF_2CF_3$, $R^8$, $OR^8$, $C(O)R^8$, $C(O)OR^8$, $SR^8$, $NH_2$, $NHR^8$, $N(R^8)_2$, $NHC(O)R^8$, $C(O)NH_2$, $C(O)NHR^8$, $C(O)N(R^8)_2$, $NHS(O)R^8$ or $NHSO_2R^8$;

$C^3$ is $S(O)R^{14}$, $SO_2R^{14}$, $S(O)R^{15}$, $SO_2R^{15}$, $S(O)R^{16}$ or $SO_2R^{16}$;

$R^8$ is $R^9$, $R^{10}$, $R^{11}$ or $R^{12}$;

$R^9$ is phenyl which is unfused or fused with benzene, heteroarene or $R^{9A}$, wherein $R^{9A}$ is cycloalkane, cycloalkene, heterocycloalkane or heterocycloalkene;

$R^{10}$ is heteroaryl which is unfused or fused with benzene, heteroarene or $R^{10A}$, wherein $R^{10A}$ is cycloalkane, cycloalkene, heterocycloalkane or heterocycloalkene;

$R^{11}$ is cycloalkyl, cycloalkenyl, heterocycloalkyl or heterocycloalkenyl, each of which is unfused or fused with benzene, heteroarene or $R^{11A}$, wherein $R^{11A}$ is cycloalkane, cycloalkene, heterocycloalkane or heterocycloalkene;

$R^{12}$ is alkyl, alkenyl or alkynyl, each of which us unsubstituted or substituted with $R^{13}$;

$R^{13}$ is phenyl, heteroaryl, cycloalkyl, cycloalkenyl, heterocycloalkyl or heterocycloalkenyl;

$R^{14}$ is perhaloalkyl or perhaloalkenyl;

$R^{15}$ is $C_1$-alkyl(methyl) or $C_2$-alkenyl(vinyl), each of which is unsubstituted or substituted with one or two of independently selected F, Cl or Br; and $R^{16}$ is $C_2$-$C_6$-alkyl, $C_3$-$C_6$-alkenyl or $C_4$-$C_6$-alkynyl, each of which is unsubstituted or substituted with one or two or three or four of independently selected F, Cl or Br;

wherein $R^2$, $R^3$, $R^4$, $R^{2A}$, $R^{3A}$, $R^{4A}$, $R^9$, $R^{10}$, $R^{11}$, $R^{9A}$, $R^{10A}$, $R^{11A}$ and $R^{13}$ are independently unsubstituted or substituted with one or two or three or four or five of independently selected $R^{17}$, $OR^{17}$, $SR^{17}$, $S(O)R^{17}$, $SO_2R^{17}$, $C(O)R^{17}$, $CO(O)R^{17}$, $OC(O)R^{17}$, $OC(O)OR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $C(O)NHOH$, $C(O)NHOR^{17}$, $C(O)NHSO_2R^{17}$, $C(O)NR^{17}NHSO_2R^{17}$, $N(SO_2R^{17})_2$, $SO_2NH_2$, $SO_2NHR^{17}$, $SO_2N(R^{17})_2$, $C(O)H$, $C(O)OH$, $C(N)NH_2$, $C(N)NHR^{17}$, $C(N)N(R^{17})_2$, $N=NR^{17}$, CNOH, $CNOCH_3$, OH, (O), $N_3$, $NO_2$, $CF_3$, $CF_2CF_3$, $CF_2Cl$, $SO_2CF_3$, $SO_2CF_2CF_3$, $SO_2CF_2Cl$, $NHSO_2CF_3$, $NHSO_2CF_2CF_3$, $OCF_3$, $OCF_2CF_3$, F, Cl, Br or I, wherein $R^{17}$ is $R^{18}$, $R^{19}$, $R^{20}$ or $R^{21}$;

$R^{18}$ is phenyl which is unfused or fused with benzene, heteroarene or $R^{18A}$, wherein $R^{18A}$ is cycloalkane, cycloalkene, heterocycloalkane or heterocycloalkene;

$R^{19}$ is heteroaryl which is unfused or fused with benzene, heteroarene or $R^{19A}$, wherein $R^{19A}$ is cycloalkane, cycloalkene, heterocycloalkane or heterocycloalkene;

$R^{20}$ is cycloalkyl, cycloalkenyl, heterocycloalkyl or heterocycloalkenyl, each of which is unfused or fused with benzene, heteroarene or $R^{20A}$, wherein $R^{20A}$ is cycloalkane, cycloalkene, heterocycloalkane or heterocycloalkene;

$R^{21}$ is alkyl, alkenyl or alkynyl, each of which is unsubstituted or substituted with one or two of independently selected alkyl, alkenyl, alkynyl, $R^{22}$, $OR^{22}$, $NHR^{22}N(R^c)R^{22}$, $SR^{22}$, $S(O)R^{22}$ or $SO_2R^{22}$;

$R^{22}$ is phenyl, heteroaryl, cycloalkyl, cycloalkenyl, heterocycloalkyl or heterocycloalkenyl, each of which is unfused or fused with, benzene, heteroarene or $R^{22A}$, wherein $R^{22A}$ is cycloalkane, cycloalkene, heterocycloalkane or heterocycloalkene;

wherein the cyclic moieties represented by $R^{18}$, $R^{18A}$, $R^{19}$, $R^{19A}$, $R^{20}$, $R^{20A}$, $R^{22}$ and $R^{22A}$ are independently unsubstituted or substituted with one or two or three or four or five of independently selected $R^{23}$, $OR^{23}$, $NHR^{23}$, $N(R^{23})_2$, $SR^{23}$, $S(O)R^{23}$ or $SO_2R^{23}$, $CF_3$, $CF_2CF_3$, $OH$, $NH_2$, $NHCH_3$, $N(CH_3)_2$, $N_3$, $NO_2$, $CF_3$, $CF_2CF_3$, $NHSO_2CF_3$, $NHSO_2CF_2CF_3$, $OCF_3$, $OCF_2CF_3$, F, Cl, Br or I;

$R^{23}$ is phenyl, heteroaryl, cycloalkyl, cycloalkenyl, heterocycloalkyl, heterocycloalkenyl or $R^{24}$;

$R^{24}$ is alkyl, alkenyl or alkynyl, each of which is unsubstituted or substituted with phenyl, heteroaryl, cycloalkyl, cycloalkenyl, heterocycloalkyl or heterocycloalkenyl.

Another embodiment pertains to compounds having formula (I), and therapeutically acceptable salts, prodrugs, salts of prodrugs and metabolites thereof, wherein $A^1$ is $A^2$, $A^3$, or $A^4$;

$A^2$ is $C_1$-$C_5$-alkyl, $C_2$-$C_5$-alkenyl or $C_2$-$C_5$-alkynyl, each of which is substituted with $R^1$ and further unsubstituted or substituted with one or two of OH;

$A^3$ is $OR^1$, $NHR^1$, $SR^1$, $SO_2R^1$, $C(O)R^1$, $L^1OR^1$, $L^1NHR^1$, $L^1SR^1$, $L^1SO_2R^1$, $L^1C(O)R^1$, $OL^1R^1$, $NHL^1R^1$, $SL^1R^1$, $SO_2L^1R^1$ or $C(O)L^1R^1$, wherein $L^1 C_1$-$C_4$-alkylene or $C_3$-$C_4$-alkenylene;

$A^4$ is $OC(O)R^1$, $C(O)OR^1$, $NHC(O)R^1$, $C(O)NHR^1$, $NHSO_2R^1$, $SO_2NHR^1$, $L^2OC(O)R^1$, $L^2C(O)OR^1$, $L^2NHC(O)R^1$, $L^2C(O)NHR^1$, $L^2NHSO_2R^1$, $L^2SO_2NHR^1$, $OC(O)L^2R^1$, $C(O)OL^2R^1$, $NHC(O)L^2R^1$, $C(O)NHL^2R^1$, $NHSO_2L^2R^1$ or $SO_2NHL^2R^1$, wherein $L^2$ is $C_1$-$C_3$-alkylene or $C_2$-$C_3$-alkenylene;

$R^1$ is $R^2$, $OR^2$, $NHR^2$, $SR^2$, $SO_2R^2$, $NHSO_2R^2$, $SO_2NHR^2$, $R^3$, $OR^3$, $NHR^3SR^3$, $SO_2R^3$, $NHSO_2R^3$, $SO_2NHR^3$ or $R^4$;

$R^2$ is phenyl which is unfused or fused with benzene, heteroarene or $R^{2A}$, wherein $R^{2A}$ is cycloalkane;

$R^3$ is heteroaryl which is unfused or fused with benzene or heteroarene;

$R^4$ is cycloalkyl fused with benzene;

$B^1$ is phenyl substituted with F;

$C^1$ is C(O)OH;

wherein the cyclic moieties represented by $R^2$, $R^{2A}$ and $R^3$ are independently unsubstituted or substituted with one or two of independently selected $R^{17}$, $OR^{17}$, $SR^{17}$, $SO_2R^{17}$, $NH_2$, $NHR^{17}$, $N(R^{17})_2$, $NHC(O)R^{17}$, $NHSO_2R^{17}$, $N(SO_2R^{17})_2$, $C(O)OH$, $N=NR^{17}$, OH, (O), $NO_2$, $CF_3$, $NHSO_2CF_3$, F, Cl, Br or I, wherein $R^{17}$ is $R^{18}$, $R^{19}$, $R^{20}$ or $R^{21}$;

$R^{18}$ is phenyl or naphthyl;

$R^{19}$ is heteroaryl which is unfused or fused with benzene;

$R^{20}$ is cycloalkyl or heterocycloalkyl;

$R^{21}$ is alkyl or alkenyl each of which is unsubstituted or substituted with one or two of independently selected alkyl, $R^{22}$, $OR^{22}$, $SR^{22}$;

$R^{22}$ is phenyl, heteroaryl or cycloalkyl, each of which is unfused or fused with heteroarene;

wherein the cyclic moieties represented by $R^{18}$, $R^{19}$, $R^{20}$ and $R^{22}$ are independently unsubstituted or substituted with one or two or three of four of independently selected $R^{23}$, $OR^{23}$, $N(R^{23})_2$, $SR^{23}$, OH or $CF_3$;

$R^{23}$ is phenyl, cycloalkyl, heterocycloalkyl or $R^{24}$;

$R^{24}$ is alkyl or alkenyl each of which is unsubstituted or substituted with phenyl or cycloalkyl.

Still another embodiment pertains to compounds having formula (I), and therapeutically acceptable salts, prodrugs, salts of prodrugs and metabolites thereof, wherein $A^1$ is $A^2$, $A^3$, or $A^4$;

$A^2$ is $C_1$-$C_5$-alkyl, $C_2$-$C_5$-alkenyl or $C_2$-$C_5$-alkynyl, each of which is substituted with $R^1$ and further unsubstituted or substituted with one or two of OH;

$A^3$ is $OR^1$, $NHR^1$, $OL^1R^1$ or $NHL^1R^1$, wherein $L^1 C_1$-$C_4$-alkylene or $C_3$-$C_4$-alkenylene;

$A^4$ is $NHC(O)R^1$, $C(O)NHR^1$, $NHSO_2R^1$, $SO_2NHR^1$, $L^2NHC(O)R^1$, $L^2C(O)NHR^1$, $L^2NHSO_2R^1$, $L^2SO_2NHR^1$, $NHC(O)L^2R^1$, $C(O)NHL^2R^1$, $NHSO_2L^2R^1$ or $SO_2NHL^2R^1$, wherein $L^2$ is $C_1$-$C_3$-alkylene or $C_2$-$C_3$-alkenylene;

$R^1$ is $R^2$, $OR^2$, $NHR^2$, $SR^2$, $SO_2R^2$, $NHSO_2R^2$, $SO_2NHR^2$, $R^3$, $OR^3$, $NHR^3SR^3$, $SO_2R^3$, $NHSO_2R^3$, $SO_2NHR^3$ or $R^4$;

$R^2$ is phenyl which is unfused or fused with benzene, heteroarene or $R^{2A}$, wherein $R^{2A}$ is cycloalkane;

$R^3$ is heteroaryl which is unfused or fused with benzene or heteroarene;

$R^4$ is cycloalkyl fused with benzene;

$B^1$ is phenyl substituted with F;

$C^1$ is C(O)OH;

Wherein the cyclic moieties represented by $R^2$, $R^{2A}$ and $R^3$ are independently unsubstituted or substituted with one or two of independently selected $R^{17}$, $OR^{17}$, $SR^{17}$, $SO_2R^{17}$, $NH_2$, $NHR^{17}$, $N(R^{17})_2$, $NHC(O)R^{17}$, $NHSO_2R^{17}$, $N(SO_2R^{17})_2$, $C(O)OH$, $N=NR^{17}$, OH, (O), $NO_2$, $CF_3$, $NHSO_2CF_3$, F, Cl, Br or I, wherein $R^{17}$ is $R^{18}$, $R^{19}$, $R^{20}$ or $R^{21}$;

$R^{18}$ is phenyl or naphthyl;

$R^{19}$ is heteroaryl which is unfused or fused with benzene;

$R^{20}$ is cycloalkyl or heterocycloalkyl;

$R^{21}$ is alkyl or alkenyl each of which is unsubstituted or substituted with one or two of independently selected alkyl, $R^{22}$, $OR^{22}$, $SR^{22}$;

$R^{22}$ is phenyl, heteroaryl or cycloalkyl, each of which is unfused or fused with heteroarene;

wherein the cyclic moieties represented by $R^{18}$, $R^{19}$, $R^{20}$ and $R^{22}$ are independently unsubstituted or substituted with one or two or three of four of independently selected $R^{23}$, $OR^{23}$, $N(R^{23})_2$, $SR^{23}$, OH or $CF_3$;

$R^{23}$ is phenyl, cycloalkyl, heterocycloalkyl or $R^{24}$;

$R^{24}$ is alkyl or alkenyl each of which is unsubstituted or substituted with phenyl or cycloalkyl.

Still another embodiment pertains to 3-((E)-2-(1,1'-biphenyl)-3-ylethenyl)-4'-fluoro(1,1'-biphenyl)-4-carboxylic acid, 3-(2-(1,1'-biphenyl)-3-ylethyl)-4'-fluoro(1,1'-biphenyl)-4-carboxylic acid, 3-((E)-2-(1,1'-biphenyl)-2-ylethenyl)-4'-fluoro(1,1'-biphenyl)-4-carboxylic acid, 4'-fluoro-3-((E)-2-(4-(((4-(trifluoromethyl)phenyl)sulfonyl)amino)phenyl)ethenyl)(1,1'-biphenyl)-4-carboxylic acid, 4'-fluoro-3-(2-(4-(((4-(trifluoromethyl)phenyl)sulfonyl)amino)phenyl)ethyl)(1,1'-biphenyl)-4-carboxylic acid, 4'-fluoro-3-((E)-2-(8-(((trifluoromethyl)sulfonyl)amino)-2-naphthyl)ethenyl)(1,1'-biphenyl)-4-carboxylic acid, 3-((E)-2-(8-amino-2-naphthyl)ethenyl)-4'-fluoro(1,1'-biphenyl)-4-carboxylic acid, 3-(2-(2-benzylphenyl)ethyl)-4'-fluoro(1,1'-biphenyl)-4-carboxylic acid, 4'-fluoro-3-((E)-2-(4-(phenoxymethyl)phenyl)ethenyl)(1,1'-biphenyl)-4-carboxylic acid, 4'-fluoro-3-((E)-2-(4-phenoxyphenyl)ethenyl)(1,1'-biphenyl)-4-carboxylic acid,
4'-fluoro-3-((E)-2-(7-hydroxy-2-naphthyl)ethenyl)(1,1'-biphenyl)-4-carboxylic acid,
3-((E)-2-(6-(cyclohexylmethoxy)-2-naphthyl)ethenyl)-4'-fluoro(1,1'-biphenyl)-4-carboxylic acid,
3-((E)-2-(4-benzylphenyl)ethenyl)-4'-fluoro(1,1'-biphenyl)-4-carboxylic acid,
4'-fluoro-3-((E)-2-(4'-propyl(1,1'-biphenyl)-4-yl)ethenyl)(1,1'-biphenyl)-4-carboxylic acid,
4'-fluoro-3-((E)-2-(3-nitro(1,1'-biphenyl)-4-yl)ethenyl)(1,1'-biphenyl)-4-carboxylic acid,
4'-fluoro-3-((4-((2-quinolinylcarbonyl)amino)phenyl)ethynyl)(1,1'-biphenyl)-4-carboxylic acid,
4'-fluoro-3-((E)-2-(4-((4-(trifluoromethyl)benzyl)amino)phenyl)ethenyl)(1,1'-biphenyl)-4-carboxylic acid,
4'-fluoro-3-((E)-2-(4-(2-naphthoylamino)phenyl)ethenyl)(1,1'-biphenyl)-4-carboxylic acid,
4'-fluoro-3-(((3-(trifluoromethyl)phenyl)sulfonyl)amino)(1,1'-biphenyl)-4-carboxylic acid,
4'-fluoro-3-((((E)-2-phenylethenyl)sulfonyl)amino)(1,1'-biphenyl)-4-carboxylic acid,
4'-fluoro-3-(((4-methylphenyl)sulfonyl)amino)(1,1'-biphenyl)-4-carboxylic acid,
4'-fluoro-3-(((4-vinylphenyl)sulfonyl)amino)(1,1'-biphenyl)-4-carboxylic acid,
4'-fluoro-3-(((4-(trifluoromethyl)phenyl)sulfonyl)amino)(1,1'-biphenyl)-4-carboxylic acid,
3-(((5-(dimethylamino)-2-naphthyl)sulfonyl)amino)-4'-fluoro(1,1'-biphenyl)-4-carboxylic acid,
3-(((4-((E)-(4-(dimethylamino)phenyl)diazenyl)phenyl)sulfonyl)amino)-4'-fluoro(1,1'-biphenyl)-4-carboxylic acid,
4'-fluoro-3-(((2-(4-pyridinyl)ethyl)sulfonyl)amino)(1,1'-biphenyl)-4-carboxylic acid,
4'-fluoro-3-((2-thienylsulfonyl)amino)(1,1'-biphenyl)-4-carboxylic acid,
3-(((4-((3-cyclohexylpropyl)amino)-3-nitrophenyl)sulfonyl)amino)-4'-fluoro(1,1'-biphenyl)-4-carboxylic acid,
4'-fluoro-3-(((3-nitro-4-((2-(phenylsulfanyl)ethyl)amino)phenyl)sulfonyl)amino)(1,1'-biphenyl)-4-carboxylic acid,
3-((2-(((4-chloro-3-nitrophenyl)sulfonyl)amino)ethyl)amino)-4'-fluoro(1,1'-biphenyl)-4-carboxylic acid,
3-((2-(((4-((cyclohexylmethyl)amino)-3-nitrophenyl)sulfonyl)amino)ethyl)amino)-4'-fluoro(1,1'-biphenyl)-4-carboxylic acid,
3-((2-(((4-((2-cyclohexylethyl)amino)-3-nitrophenyl)sulfonyl)amino)ethyl)amino)-4'-fluoro(1,1'-biphenyl)-4-carboxylic acid,
3-((4-((3-cyclohexylpropyl)amino)-3-nitrobenzyl)amino)-4'-fluoro(1,1'-biphenyl)-4-carboxylic acid,
4'-fluoro-3-((2-(8-hydroxy-5,6,7,8-tetrahydro-2-naphthalenyl)ethyl)amino)(1,1'-biphenyl)-4-carboxylic acid,
4'-fluoro-3-(3-(2-hydroxyphenyl)propoxy)(1,1'-biphenyl)-4-carboxylic acid,
4'-fluoro-3-(3-(5,6,7,8-tetrahydro-1-naphthalenyloxy)propoxy)(1,1'-biphenyl)-4-carboxylic acid and
4'-fluoro-3-(((2E)-4-(1-naphthyl)-2-butenyl)oxy)(1,1'-biphenyl)-4-carboxylic acid
4'-fluoro-3-((3-nitro-4-(2-propylphenoxy)benzoyl)amino)(1,1'-biphenyl)-4-carboxylic acid,
3-((4-((cyclohexylmethyl)amino)-3-nitrobenzoyl)amino)-4'-fluoro(1,1'-biphenyl)-4-carboxylic acid,
3-((4-((1-adamantylmethyl)amino)-3-nitrobenzoyl)amino)-4'-fluoro(1,1'-biphenyl)-4-carboxylic acid,
4'-fluoro-3-((3-nitro-4-((2-(phenylsulfanyl)ethyl)amino)benzoyl)amino)(1,1'-biphenyl)-4-carboxylic acid,
3-((4-((2-(cyclohexylsulfanyl)ethyl)amino)-3-nitrobenzoyl)amino)-4'-fluoro(1,1'-biphenyl)-4-carboxylic acid,
4'-fluoro-3-((3-nitro-4-((2-(phenylsulfanyl)ethyl)amino)anilino)carbonyl)(1,1'-biphenyl)-4-carboxylic acid,
3-((4-((1-adamantylmethyl)amino)-3-nitroanilino)carbonyl)-4'-fluoro(1,1'-biphenyl)-4-carboxylic acid,
3-((4-((cyclohexylmethyl)amino)-3-nitroanilino)carbonyl)-4'-fluoro(1,1'-biphenyl)-4-carboxylic acid,
4'-fluoro-3-(((5-hydroxy-2-naphthyl)amino)carbonyl)(1,1'-biphenyl)-4-carboxylic acid,
4'-fluoro-3-(3-(6-hydroxy-2-naphthyl)propyl)(1,1'-biphenyl)-4-carboxylic acid,
4'-fluoro-3-((1E)-4-(6-hydroxy-2-naphthyl)-1-butenyl)(1,1'-biphenyl)-4-carboxylic acid,
4'-fluoro-3-(4-(6-hydroxy-2-naphthyl)butyl)(1,1'-biphenyl)-4-carboxylic acid,
4'-fluoro-3-(5-(6-hydroxy-2-naphthyl)pentyl)(1,1'-biphenyl)-4-carboxylic acid,
4'-fluoro-3-(5-(6-hydroxy-5,6,7,8-tetrahydro-2-naphthalenyl)pentyl)(1,1'-biphenyl)-4-carboxylic acid,
4'-fluoro-3-((1E)-4-(7-methoxy-1-naphthyl)-1-butenyl)(1,1'-biphenyl)-4-carboxylic acid,
4'-fluoro-3-((1E)-4-(7-hydroxy-1-naphthyl)-1-butenyl)(1,1'-biphenyl)-4-carboxylic acid,
4'-fluoro-3-(4-(7-methoxy-1-naphthyl)butyl)(1,1'-biphenyl)-4-carboxylic acid,
4'-fluoro-3-(4-(7-hydroxy-1-naphthyl)butyl)(1,1'-biphenyl)-4-carboxylic acid,
3-((E)-2-(3-(benzylamino)-4-((3-cyclohexylpropyl)amino)phenyl)ethenyl)-4'-fluoro(1,1'-biphenyl)-4-carboxylic acid,
3-((E)-2-(4-((3-cyclohexylpropyl)amino)-3-nitrophenyl)ethenyl)-4'-fluoro(1,1'-biphenyl)-4-carboxylic acid,
3-((E)-2-(1-(3-cyclohexylpropyl)-1H-1,2,3-benzotriazol-5-yl)ethenyl)-4'-fluoro(1,1'-biphenyl)-4-carboxylic acid,
3-((E)-2-(4-(cyclohexylamino)-3-nitrophenyl)ethenyl)-4'-fluoro(1,1'-biphenyl)-4-carboxylic acid,
3-((E)-2-(4-((4-chlorophenyl)sulfanyl)-3-nitrophenyl)ethenyl)-4'-fluoro(1,1'-biphenyl)-4-carboxylic acid,
3-((E)-2-(4-((cyclohexylmethyl)amino)-3-nitrophenyl)ethenyl)-4'-fluoro(1,1'-biphenyl)-4-carboxylic acid,
4'-fluoro-3-((E)-2-(3-nitro-4-(1-piperidinyl)phenyl)ethenyl)(1,1'-biphenyl)-4-carboxylic acid,
4'-fluoro-3-((E)-2-(3-nitro-4-phenoxyphenyl)ethenyl)(1,1'-biphenyl)-4-carboxylic acid,
4'-fluoro-3-((E)-2-(3-nitro-4-(5,6,7,8-tetrahydro-1-naphthalenyloxy)phenyl)ethenyl)(1,1'-biphenyl)-4-carboxylic acid,
4'-fluoro-3-((E)-2-(4-((2-(1H-indol-2-yl)ethyl)amino)-3-nitrophenyl)ethenyl)(1,1'-biphenyl)-4-carboxylic acid,
3-((E)-2-(4-(benzyl(2-phenylethyl)amino)-3-nitrophenyl)ethenyl)-4'-fluoro(1,1'-biphenyl)-4-carboxylic acid,
4'-fluoro-3-((E)-2-(3-nitro-4-((2-(phenylsulfanyl)ethyl)amino)phenyl)ethenyl)(1,1'-biphenyl)-4-carboxylic acid,
3-((E)-2-(4-(4-cyclopentylphenoxy)-3-nitrophenyl)ethenyl)-4'-fluoro(1,1'-biphenyl)-4-carboxylic acid,
3-((E)-2-(4-(3-tert-butylphenoxy)-3-nitrophenyl)ethenyl)-4'-fluoro(1,1'-biphenyl)-4-carboxylic acid,
4'-fluoro-3-((E)-2-(4-(2-(4-morpholinyl)phenoxy)-3-nitrophenyl)ethenyl)(1,1'-biphenyl)-4-carboxylic acid,
3-((E)-2-(4-(2-benzyl-4-methylphenoxy)-3-nitrophenyl)ethenyl)-4'-fluoro(1,1'-biphenyl)-4-carboxylic acid,
3-((E)-2-(4-(2-tert-butylphenoxy)-3-nitrophenyl)ethenyl)-4'-fluoro(1,1'-biphenyl)-4-carboxylic acid,
4'-fluoro-3-((E)-2-(3-nitro-4-(2-(trifluoromethyl)phenoxy)phenyl)ethenyl)(1,1'-biphenyl)-4-carboxylic acid, 3-((E)-2-(4-((1-cyclohexyl-2-propenyl)oxy)-3-nitrophenyl)ethenyl)-4'-fluoro(1,1'-biphenyl)-4-carboxylic acid, 3-((E)-2-(4-((3-cyclohexylpropyl)(3-phenylpropyl)amino)-3-nitrophenyl)ethenyl)-4'-fluoro(1,1'-biphenyl)-4-carboxylic acid, 4'-fluoro-3-((E)-2-(3-nitro-4-(1,2,3,4-tetrahydro-1-naphthalenyloxy)phenyl)ethenyl)(1,1'-biphenyl)-4-carboxylic acid, 3-((E)-2-(4-(4-cyclohexylbutoxy)-3-nitrophenyl)ethenyl)-4'-fluoro(1,1'-biphenyl)-4-carboxylic acid, 4'-fluoro-3-((E)-2-(3-nitro-4-(4-phenylbutoxy)phenyl)ethenyl)(1,1'-biphenyl)-4-carboxylic acid, 3-((E)-2-(4-(cyclohexyloxy)-3-nitrophenyl)ethenyl)-4'-fluoro(1,1'-biphenyl)-4-carboxylic acid, 4'-fluoro-3-(2-(7-hydroxy-1-naphthyl)ethyl)(1,1'-biphenyl)-4-carboxylic acid, 4'-fluoro-3-(3-(8-hydroxy-2-naphthyl)propyl)(1,1'-biphenyl)-4-carboxylic acid, 4'-fluoro-3-(3-(7-hydroxy-1-naphthyl)propyl)(1,1'-biphenyl)-4-carboxylic acid, 4'-fluoro-3-((E)-2-(8-hydroxy-2-naphthyl)ethenyl)(1,1'-biphenyl)-4-carboxylic acid, 4'-fluoro-3-((E)-2-(7-hydroxy-1-naphthyl)ethenyl)(1,1'-biphenyl)-4-carboxylic acid 4'-fluoro-3-((1E)-3-(8-hydroxy-2-naphthyl)-1-propenyl)(1,1'-biphenyl)-4-carboxylic acid, 4'-fluoro-3-((1E)-3-(7-hydroxy-1-naphthyl)-1-propenyl)(1,1'-biphenyl)-4-carboxylic acid 4'-fluoro-3-(2-(8-hydroxy-2-naphthyl)ethyl)(1,1'-biphenyl)-4-carboxylic acid, 4'-fluoro-3-((E)-2-(6-hydroxy-2-naphthyl)ethenyl)(1,1'-biphenyl)-4-carboxylic acid, 4'-fluoro-3-(2-(6-hydroxy-5,6,7,8-tetrahydro-2-naphthalenyl)ethyl)(1,1'-biphenyl)-4-carboxylic acid, 4'-fluoro-3-(2-(6-hydroxy-2-naphthyl)ethyl)(1,1'-biphenyl)-4-carboxylic acid, 4'-fluoro-3-(((7-hydroxy-1-naphthyl)amino)carbonyl)(1,1'-biphenyl)-4-carboxylic acid, 4'-fluoro-3-((E)-2-(7-hydroxy-1-naphthyl)ethenyl)(1,1'-biphenyl)-4-carboxylic acid, 4'-fluoro-3-((E)-2-(7-methoxy-1-naphthyl)ethenyl)(1,1'-biphenyl)-4-carboxylic acid, 4'-fluoro-3-(((2E)-3-(8-hydroxy-2-naphthyl)-2-propenoyl)amino)(1,1'-biphenyl)-4-carboxylic acid, 4'-fluoro-3-((8-hydroxy-2-naphthoyl)amino)(1,1'-biphenyl)-4-carboxylic acid, 4'-fluoro-3-((E)-2-(8-hydroxy-5,6,7,8-tetrahydro-2-naphthalenyl)ethenyl)(1,1'-biphenyl)-4-carboxylic acid, 4'-fluoro-3-((E)-2-(8-hydroxy-2-naphthyl)ethenyl)(1,1'-biphenyl)-4-carboxylic acid, 3-((3,5-dimethoxy-2-naphthoyl)amino)-4'-fluoro(1,1'-biphenyl)-4-carboxylic acid, 4'-fluoro-3-((E)-2-(8-oxo-5,6,7,8-tetrahydro-2-naphthalenyl)ethenyl)(1,1'-biphenyl)-4-carboxylic acid, 4'-fluoro-3-(((8-hydroxy-2-naphthyl)methyl)amino)(1,1'-biphenyl)-4-carboxylic acid, 3-(1,2-dihydroxy-2-(8-hydroxy-2-naphthyl)ethyl)-4'-fluoro(1,1'-biphenyl)-4-carboxylic acid, 4'-fluoro-3-((3-(8-hydroxy-2-naphthyl)propanoyl)amino)(1,1'-biphenyl)-4-carboxylic acid, 3-((E)-2-(4-bromo-3-carboxyphenyl)ethenyl)-4'-fluoro(1,1'-biphenyl)-4-carboxylic acid, 6-((E)-2-(4-carboxy-4'-fluoro(1,1'-biphenyl)-3-yl)ethenyl)-1-naphthoic acid, 6-(2-(4-carboxy-4'-fluoro(1,1'-biphenyl)-3-yl)ethyl)-1-naphthoic acid, 4'-fluoro-3-(((8-hydroxy-2-naphthyl)amino)carbonyl)(1,1'-biphenyl)-4-carboxylic acid, 4'-fluoro-3-((2-(8-hydroxy-5,6,7,8-tetrahydro-2-naphthalenyl)ethyl)amino)(1,1'-biphenyl)-4-carboxylic acid, 4'-fluoro-3-((8-hydroxy-2-naphthyl)ethynyl)(1,1'-biphenyl)-4-carboxylic acid, 4'-fluoro-3-(2-((8-hydroxy-2-naphthyl)amino)-2-oxoethyl)(1,1'-biphenyl)-4-carboxylic acid, 3-(((1,1'-biphenyl)-4-ylsulfonyl)amino)-4'-fluoro(1,1'-biphenyl)-4-carboxylic acid, 4'-fluoro-3-((2-naphthylsulfonyl)amino)(1,1'-biphenyl)-4-carboxylic acid, 4'-fluoro-3-((phenylsulfonyl)amino)(1,1'-biphenyl)-4-carboxylic acid, 4'-fluoro-3-((1-naphthylsulfonyl)amino)(1,1'-biphenyl)-4-carboxylic acid, 4'-fluoro-3-(((8-hydroxy-2-naphthyl)acetyl)amino)(1,1'-biphenyl)-4-carboxylic acid, 3-((E)-2-(4-(carboxy(hydroxy)methyl)phenyl)ethenyl)-4'-fluoro(1,1'-biphenyl)-4-carboxylic acid, 6-((E)-2-(4-carboxy-4'-fluoro(1,1'-biphenyl)-3-yl)ethenyl)-2-naphthoic acid, 4'-fluoro-3-((6-hydroxy-2-naphthoyl)amino)(1,1'-biphenyl)-4-carboxylic acid, 4'-fluoro-3-(2-(2-naphthyl)ethyl)(1,1'-biphenyl)-4-carboxylic acid, 3-(2-(4-(carboxy(hydroxy)methyl)phenyl)ethyl)-4'-fluoro(1,1'-biphenyl)-4-carboxylic acid, 6-(2-(4-carboxy-4'-fluoro(1,1'-biphenyl)-3-yl)ethyl)-2-naphthoic acid, 3-((E)-2-(4-carboxyphenyl)ethenyl)-4'-fluoro(1,1'-biphenyl)-4-carboxylic acid, 4'-fluoro-3-((E)-2-(6-hydroxy-5,6,7,8-tetrahydro-2-naphthalenyl)ethenyl)(1,1'-biphenyl)-4-carboxylic acid, 3-(2-(4-carboxyphenyl)ethyl)-4'-fluoro(1,1'-biphenyl)-4-carboxylic acid, 4'-fluoro-3-((E)-2-(3-(((4-(trifluoromethyl)phenyl)sulfonyl)amino)phenyl)ethenyl)(1,1'-biphenyl)-4-carboxylic acid, 4'-fluoro-3-(2-(3-(((4-(trifluoromethyl)phenyl)sulfonyl)amino)phenyl)ethyl)(1,1'-biphenyl)-4-carboxylic acid, 4'-fluoro-3-(2-(6-hydroxy-1,2,3,4-tetrahydro-2-naphthalenyl)ethyl)(1,1'-biphenyl)-4-carboxylic acid, 4'-fluoro-3-(2-(4-((4-(trifluoromethyl)anilino)sulfonyl)phenyl)ethyl)(1,1'-biphenyl)-4-carboxylic acid, 4'-fluoro-3-((E)-2-(4-((4-(trifluoromethyl)anilino)sulfonyl)phenyl)ethenyl)(1,1'-biphenyl)-4-carboxylic acid, 4'-fluoro-3-((1E)-5-(6-hydroxy-2-naphthyl)-1-pentenyl)(1,1'-biphenyl)-4-carboxylic acid, 4'-fluoro-3-(3-(6-hydroxy-5,6,7,8-tetrahydro-2-naphthalenyl)propyl)(1,1'-biphenyl)-4-carboxylic acid, 4'-fluoro-3-(4-(6-hydroxy-5,6,7,8-tetrahydro-2-naphthalenyl)butyl)(1,1'-biphenyl)-4-carboxylic acid, 4'-fluoro-3-((1E)-3-(6-hydroxy-2-naphthyl)-1-propenyl)(1,1'-biphenyl)-4-carboxylic acid, 4'-fluoro-3-((2E)-3-(6-hydroxy-2-naphthyl)-2-propenyl)(1,1'-biphenyl)-4-carboxylic acid, 4'-fluoro-3-(2-(8-(((4-methylphenyl)sulfonyl)amino)-2-naphthyl)ethyl)(1,1'-biphenyl)-4-carboxylic acid, 4'-fluoro-3-((E)-2-(8-(((4-methylphenyl)sulfonyl)amino)-2-naphthyl)ethenyl)(1,1'-biphenyl)-4-carboxylic acid, 3-((E)-2-(1,1'-biphenyl)-4-ylethenyl)-4'-fluoro(1,1'-biphenyl)-4-carboxylic acid, 3-(2-(1,1'-biphenyl)-4-ylethyl)-4'-fluoro(1,1'-biphenyl)-4-carboxylic acid, 3-((E)-2-(2-benzylphenyl)ethenyl)-4'-fluoro(1,1'-biphenyl)-4-carboxylic acid, 4'-fluoro-3-((E)-2-(5-hydroxy-2-naphthyl)ethenyl)(1,1'-biphenyl)-4-carboxylic acid,
4'-fluoro-3-((E)-2-(5-hydroxy-1-naphthyl)ethenyl)(1,1'-biphenyl)-4-carboxylic acid,
4'-fluoro-3-((1E)-4-(6-hydroxy-1-naphthyl)-1-butenyl)(1,1'-biphenyl)-4-carboxylic acid,
4'-fluoro-3-(4-(6-hydroxy-1-naphthyl)butyl)(1,1'-biphenyl)-4-carboxylic acid,
4'-fluoro-3-((1E)-4-(6-methoxy-1-naphthyl)-1-butenyl)(1,1'-biphenyl)-4-carboxylic acid,
3-((E)-2-(3-(benzyloxy)phenyl)ethenyl)-4'-fluoro(1,1'-biphenyl)-4-carboxylic acid,
3-((E)-2-(9H-fluoren-2-yl)ethenyl)-4'-fluoro(1,1'-biphenyl)-4-carboxylic acid,
3-((E)-2-(4-(benzyloxy)phenyl)ethenyl)-4'-fluoro(1,1'-biphenyl)-4-carboxylic acid,
3-((E)-2-(1,1'-biphenyl)-4-ylethenyl)(1,1'-biphenyl)-4-carboxylic acid,
4'-fluoro-3-((E)-2-(2'-nitro(1,1'-biphenyl)-4-yl)ethenyl)(1,1'-biphenyl)-4-carboxylic acid,
4'-fluoro-3-((E)-2-(1-((4-methylphenyl)sulfonyl)-1H-indol-5-yl)ethenyl)(1,1'-biphenyl)-4-carboxylic acid,
4'-fluoro-3-((E)-2-(1-((4-methylphenyl)sulfonyl)-1H-indol-6-yl)ethenyl)(1,1'-biphenyl)-4-carboxylic acid,
3-((E)-2-(4-cyclohexylphenyl)ethenyl)-4'-fluoro(1,1'-biphenyl)-4-carboxylic acid,
4'-fluoro-3-((E)-2-(4'-fluoro(1,1'-biphenyl)-4-yl)ethenyl)(1,1'-biphenyl)-4-carboxylic acid,
4'-fluoro-3-((E)-2-(3-(4-fluorophenoxy)phenyl)ethenyl)(1,1'-biphenyl)-4-carboxylic acid,
4'-fluoro-3-((E)-2-(1H-indol-6-yl)ethenyl)(1,1'-biphenyl)-4-carboxylic acid,
4'-fluoro-3-((E)-2-(4-((2-methyl-1H-imidazo[4,5-c]pyridin-1-yl)methyl)phenyl)ethenyl)(1,1'-biphenyl)-4-carboxylic acid,
4'-fluoro-3-((E)-2-(1H-indol-5-yl)ethenyl)(1,1'-biphenyl)-4-carboxylic acid,
3-((E)-2-(4-(4,6-diamino-1,3,5-triazin-2-yl)phenyl)ethenyl)-4'-fluoro(1,1'-biphenyl)-4-carboxylic acid,
3-((4-(4,6-diamino-1,3,5-triazin-2-yl)phenyl)ethynyl)-4'-fluoro(1,1'-biphenyl)-4-carboxylic acid,
4'-fluoro-3-((4-((2-methyl-1H-imidazo[4,5-c]pyridin-1-yl)methyl)phenyl)ethynyl)(1,1'-biphenyl)-4-carboxylic acid,
4'-fluoro-3-((E)-2-(4-((E)-2-phenylethenyl)phenyl)ethenyl)(1,1'-biphenyl)-4-carboxylic acid,
4'-fluoro-3-(2-(4-(2-phenylethyl)phenyl)ethyl)(1,1'-biphenyl)-4-carboxylic acid,
4'-fluoro-3-(4-isoquinolinylethynyl)(1,1'-biphenyl)-4-carboxylic acid,
4'-fluoro-3-(3-quinolinylethynyl)(1,1'-biphenyl)-4-carboxylic acid,
4'-fluoro-3-(1H-indol-5-ylethynyl)(1,1'-biphenyl)-4-carboxylic acid,
3-((E)-2-(4-(1-benzothien-2-yl)phenyl)ethenyl)-4'-fluoro(1,1'-biphenyl)-4-carboxylic acid,
4'-fluoro-3-((E)-2-(4-(1H-imidazol-1-yl)phenyl)ethenyl)(1,1'-biphenyl)-4-carboxylic acid,
4'-fluoro-3-((3-(1-naphthyl)phenyl)ethynyl)(1,1'-biphenyl)-4-carboxylic acid,
4'-fluoro-3-((4-(1-naphthyl)phenyl)ethynyl)(1,1'-biphenyl)-4-carboxylic acid,
3-((3-bromophenyl)ethynyl)-4'-fluoro(1,1'-biphenyl)-4-carboxylic acid,
3-((4-bromophenyl)ethynyl)-4'-fluoro(1,1'-biphenyl)-4-carboxylic acid,
4'-fluoro-3-((4-(((4-(trifluoromethyl)phenyl)sulfonyl)amino)phenyl)ethynyl)(1,1'-biphenyl)-4-carboxylic acid,
4'-fluoro-3-((4-((4-(trifluoromethyl)benzoyl)amino)phenyl)ethynyl)(1,1'-biphenyl)-4-carboxylic acid,
3-((4-aminophenyl)ethynyl)-4'-fluoro(1,1'-biphenyl)-4-carboxylic acid,
4'-fluoro-3-((4-((4-methylbenzoyl)amino)phenyl)ethynyl)(1,1'-biphenyl)-4-carboxylic acid,
3-((E)-2-(4-(4-butyl-1-piperazinyl)phenyl)ethenyl)-4'-fluoro(1,1'-biphenyl)-4-carboxylic acid,
4'-fluoro-3-((E)-2-(3-nitro(1,1'-biphenyl)-4-yl)ethenyl)(1,1'-biphenyl)-4-carboxylic acid,
3-((4-((3,5-difluorobenzoyl)amino)phenyl)ethynyl)-4'-fluoro(1,1'-biphenyl)-4-carboxylic acid,
4'-fluoro-3-((E)-2-(4-(3-pyridinyl)phenyl)ethenyl)(1,1'-biphenyl)-4-carboxylic acid,
4'-fluoro-3-((4-(2-naphthoylamino)phenyl)ethynyl)(1,1'-biphenyl)-4-carboxylic acid,
4'-fluoro-3-((4-(((4-methylphenyl)sulfonyl)amino)phenyl)ethynyl)(1,1'-biphenyl)-4-carboxylic acid,
3-((4-(bis((4-methylphenyl)sulfonyl)amino)phenyl)ethynyl)-4'-fluoro(1,1'-biphenyl)-4-carboxylic acid,
4'-fluoro-3-(2-(4-((2-quinolinylcarbonyl)amino)phenyl)ethyl)(1,1'-biphenyl)-4-carboxylic acid,
4'-fluoro-3-(2-(4-(2-naphthoylamino)phenyl)ethyl)(1,1'-biphenyl)-4-carboxylic acid,
4'-fluoro-3-((4-(2-furyl)phenyl)ethynyl)(1,1'-biphenyl)-4-carboxylic acid,
4'-fluoro-3-((3-(2-furyl)phenyl)ethynyl)(1,1'-biphenyl)-4-carboxylic acid,
4'-fluoro-3-((4-(3-pyridinyl)phenyl)ethynyl)(1,1'-biphenyl)-4-carboxylic acid,
4'-fluoro-3-((3-(3-pyridinyl)phenyl)ethynyl)(1,1'-biphenyl)-4-carboxylic acid,
4'-fluoro-3-((3-(3-furyl)phenyl)ethynyl)(1,1'-biphenyl)-4-carboxylic acid,
4'-fluoro-3-((4-(3-furyl)phenyl)ethynyl)(1,1'-biphenyl)-4-carboxylic acid,
4'-fluoro-3-((4-(4-pyridinyl)phenyl)ethynyl)(1,1'-biphenyl)-4-carboxylic acid,
4'-fluoro-3-((3-(2-pyridinyl)phenyl)ethynyl)(1,1'-biphenyl)-4-carboxylic acid,
4'-fluoro-3-((3-(4-pyridinyl)phenyl)ethynyl)(1,1'-biphenyl)-4-carboxylic acid,
3-((E)-2-(4-(cyclohexylamino)-3-nitrophenyl)ethenyl)-4'-fluoro(1,1'-biphenyl)-4-carboxylic acid,
4'-fluoro-3-(2-(4-(3-pyridinyl)phenyl)ethyl)(1,1'-biphenyl)-4-carboxylic acid,
3-((E)-2-(4-anilino-3-nitrophenyl)ethenyl)-4'-fluoro(1,1'-biphenyl)-4-carboxylic acid,
4'-fluoro-3-((E)-2-(2-fluoro(1,1'-biphenyl)-4-yl)ethenyl)(1,1'-biphenyl)-4-carboxylic acid,
4'-fluoro-3-((E)-2-(4-((2-quinolinylcarbonyl)amino)phenyl)ethenyl)(1,1'-biphenyl)-4-carboxylic acid,
3-((1,1'-biphenyl)-3-ylethynyl)-4'-fluoro(1,1'-biphenyl)-4-carboxylic acid,
4'-fluoro-3-((3-((4-(trifluoromethyl)benzyl)amino)phenyl)ethynyl)(1,1'-biphenyl)-4-carboxylic acid,
4'-fluoro-3-((3-(2-naphthoylamino)phenyl)ethynyl)(1,1'-biphenyl)-4-carboxylic acid,
3-((E)-2-(4-((1-cyclohexylethyl)amino)-3-nitrophenyl)ethenyl)-4'-fluoro(1,1'-biphenyl)-4-carboxylic acid,
4'-fluoro-3-((Z)-2-(4-((4-(trifluoromethyl)benzyl)amino)phenyl)ethenyl)(1,1'-biphenyl)-4-carboxylic acid,
4'-fluoro-3-(2-(4-((4-(trifluoromethyl)benzyl)amino)phenyl)ethyl)(1,1'-biphenyl)-4-carboxylic acid,
3-((1,1'-biphenyl)-4-ylethynyl)-4'-fluoro(1,1'-biphenyl)-4-carboxylic acid, 3-((E)-2-(4-((2-cyclohexylethyl)amino)-3-nitrophenyl)ethenyl)-4'-fluoro(1,1'-biphenyl)-4-carboxylic acid, 4'-fluoro-3-((E)-2-(3-nitro-4-(5,6,7,8-tetrahydro-1-naphthalenylamino)phenyl)ethenyl)(1,1'-biphenyl)-4-carboxylic acid, 4'-fluoro-3-((E)-2-(3-nitro-4-((2-phenylethyl)amino)phenyl)ethenyl)(1,1'-biphenyl)-4-carboxylic acid, 3-((E)-2-(4-(cycloheptylamino)-3-nitrophenyl)ethenyl)-4'-fluoro(1,1'-biphenyl)-4-carboxylic acid, 3-((2-(((4-(cyclohexylamino)-3-nitrophenyl)sulfonyl)amino)ethyl)amino)-4'-fluoro(1,1'-biphenyl)-4-carboxylic acid, 4'-fluoro-3-((E)-2-(6-phenoxy-2-naphthyl)ethenyl)(1,1'-biphenyl)-4-carboxylic acid, 4'-fluoro-3-((E)-2-(4-(2-isopropoxyphenoxy)-3-nitrophenyl)ethenyl)(1,1'-biphenyl)-4-carboxylic acid, 4'-fluoro-3-((2-(((3-nitro-4-((2-(phenylsulfanyl)ethyl)amino)phenyl)sulfonyl)amino)ethyl)amino)(1,1'-biphenyl)-4-carboxylic acid, 3-((E)-2-(4-(2,3-dimethoxyphenoxy)-3-nitrophenyl)ethenyl)-4'-fluoro(1,1'-biphenyl)-4-carboxylic acid, 3-((E)-2-(4-(2-((2Z)-2-butenyl)phenoxy)-3-nitrophenyl)ethenyl)-4'-fluoro(1,1'-biphenyl)-4-carboxylic acid, 3-((E)-2-(4-(2-(benzyloxy)phenoxy)-3-nitrophenyl)ethenyl)-4'-fluoro(1,1'-biphenyl)-4-carboxylic acid, 4'-fluoro-3-((E)-2-(3-nitro-4-(2-propylphenoxy)phenyl)ethenyl)(1,1'-biphenyl)-4-carboxylic acid, 3-((E)-2-(4-(4-chloro-2-cyclohexylphenoxy)-3-nitrophenyl)ethenyl)-4'-fluoro(1,1'-biphenyl)-4-carboxylic acid, 4'-fluoro-3-((E)-2-(4-(2-(methylsulfanyl)phenoxy)-3-nitrophenyl)ethenyl)(1,1'-biphenyl)-4-carboxylic acid, 3-((E)-2-(4-((1-adamantylmethyl)amino)-3-nitrophenyl)ethenyl)-4'-fluoro(1,1'-biphenyl)-4-carboxylic acid, 4'-fluoro-3-((E)-2-(3-nitro-4-(5,6,7,8-tetrahydro-2-naphthalenyloxy)phenyl)ethenyl)(1,1'-biphenyl)-4-carboxylic acid, 4'-fluoro-3-((E)-2-(3-nitro-4-(4-phenyl-1-piperazinyl)phenyl)ethenyl)(1,1'-biphenyl)-4-carboxylic acid, 3-((E)-2-(4-(dibutylamino)-3-nitrophenyl)ethenyl)-4'-fluoro(1,1'-biphenyl)-4-carboxylic acid, 3-((E)-2-(4-(3,5-ditert-butylphenoxy)-3-nitrophenyl)ethenyl)-4'-fluoro(1,1'-biphenyl)-4-carboxylic acid, 4'-fluoro-3-((E)-2-(4-(2-isopropylphenoxy)-3-nitrophenyl)ethenyl)(1,1'-biphenyl)-4-carboxylic acid, 3-((4-(2-tert-butylphenoxy)-3-nitrobenzoyl)amino)-4'-fluoro(1,1'-biphenyl)-4-carboxylic acid, 4-((4-(2-tert-butylphenoxy)-3-nitrobenzoyl)amino)-4'-fluoro(1,1'-biphenyl)-3-carboxylic acid, 4'-fluoro-3-((E)-2-(4-(2-hydroxyphenoxy)-3-nitrophenyl)ethenyl)(1,1'-biphenyl)-4-carboxylic acid, 4'-fluoro-3-((E)-2-(3-nitro-4-(octylamino)phenyl)ethenyl)(1,1'-biphenyl)-4-carboxylic acid, 4'-fluoro-3-((E)-2-(4-(2-fluorophenoxy)-3-nitrophenyl)ethenyl)(1,1'-biphenyl)-4-carboxylic acid, 4'-fluoro-3-((E)-2-(3-nitro-4-((5,5,8,8-tetramethyl-5,6,7,8-tetrahydro-1-naphthalenyl)oxy)phenyl)ethenyl)(1,1'-biphenyl)-4-carboxylic acid, 3-((E)-2-(4-((5,5-dimethyl-5,6,7,8-tetrahydro-1-naphthalenyl)oxy)-3-nitrophenyl)ethenyl)-4'-fluoro(1,1'-biphenyl)-4-carboxylic acid, 3-((E)-2-(4-(dicyclohexylmethoxy)-3-nitrophenyl)ethenyl)-4'-fluoro(1,1'-biphenyl)-4-carboxylic acid, and therapeutically acceptable salts, prodrugs, salts of prodrugs and metabolites thereof.

Still another embodiment pertains to compositions for treating diseases during which are expressed anti-apoptotic Mcl-1 protein, said compositions comprising an excipient and a therapeutically effective amount of the compound having formula (I).

Still another embodiment pertains to methods of treating diseases in a patient during which are expressed anti-apoptotic Mcl-1 protein, said methods comprising administering to the patient a therapeutically effective amount of a compound having formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer, said compositions comprising an excipient and a therapeutically effective amount of the compound having formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer in a patient, said methods comprising administering to the patient a therapeutically effective amount of a compound having formula (I).

Still another embodiment pertains to compositions for treating diseases in a patient during which are expressed anti-apoptotic Mcl-1 protein, said compositions comprising an excipient and a therapeutically effective amount of the compound having formula (I) and a therapeutically effective amount of one additional therapeutic agent or more than one additional therapeutic agent.

Still another embodiment pertains to methods of treating diseases in a patient during which is expressed anti-apoptotic Mcl-1 protein, said methods comprising administering to the patient a therapeutically effective amount of a compound having formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of the compound having formula (I) and a therapeutically effective amount of one additional therapeutic agent or more than one additional therapeutic agent.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends, and that divalent moieties are drawn from left to right.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

The term "cycloalkane," as used herein, means $C_3$-cycloalkane, $C_4$-cycloalkane, $C_5$-cycloalkane, $C_6$-cycloalkane, $C_7$-cycloalkane, $C_8$-cycloalkane, $C_9$-cycloalkane and $C_{10}$-cycloalkane.

The term "cycloalkyl," as used herein, means $C_3$-cycloalkyl, $C_4$-cycloalkyl, $C_5$-cycloalkyl $C_6$-cycloalkyl, $C_7$-cycloalkyl, $C_8$-cycloalkyl, $C_9$-cycloalkyl and $C_{10}$-cycloalkyl.

The term "cycloalkene," as used herein, means $C_4$-cycloalkene, $C_5$-cycloalkene, $C_6$-cycloalkene, $C_7$-cycloalkene, $C_8$-cycloalkene, $C_9$-cycloalkene and $C_{10}$-cycloalkene.

The term "cycloalkenyl," as used herein, means $C_3$-cycloalkenyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl and $C_{10}$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "$C_2$-$C_5$-alkenyl," as used herein, means $C_2$-alkenyl, $C_3$-alkenyl, $C_4$-alkenyl and $C_5$-alkenyl.

The term "$C_2$-$C_3$-alkenylene," as used herein, means $C_2$-alkenylene and $C_3$-alkyenlene.

The term "alkyl," as used herein, means $C_1$-alkyl, $C_2$-alkyl, $C_3$-alkyl, $C_4$-alkyl, $C_5$-alkyl and $C_6$-alkyl.

The term "$C_1$-$C_5$-alkyl," as used herein, means $C_1$-alkyl, $C_2$-alkyl, $C_3$-alkyl, $C_4$-alkyl and $C_5$-alkyl.

The term "$C_1$-$C_3$-alkylene," as used herein, means $C_1$-alkylene, $C_2$-alkylene and $C_3$-alkylene.

The term "$C_1$-$C_4$-alkylene," as used herein, means $C_1$-alkylene, $C_2$-alkylene, $C_3$-alkylene and $C_4$-alkylene.

The term "alkynyl," as used herein, means $C_2$-alkynyl, $C_3$-alkynyl, $C_4$-alkynyl, $C_5$-alkynyl and $C_6$-alkynyl.

The term "$C_2$-$C_5$-alkynyl," as used herein, means $C_2$-alkynyl, $C_3$-alkynyl, $C_4$-alkynyl and $C_5$-alkynyl.

The term "$C_2$-alkenyl," as used herein, means ethenyl(vinyl).

The term "$C_3$-alkenyl," as used herein, means 1-propen-1-yl, 1-propen-2-yl (isopropenyl) and 1-propen-3-yl(allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylene-pent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_2$-alkenylene," as used herein, means ethen-1,2-ylene, the ends of which are attached to different atoms.

The term "$C_3$-alkenylene," as used herein, means prop-1-en-1,3-ylene and prop-2-en-1,3-ylene, the ends of each of which are attached to different atoms.

The term "$C_4$-alkenylene," as used herein, means but-1-en-1,4-ylene, but-2-en-1,4-ylene and buta-1,3-dien-1,4-ylene, the ends of each of which are attached to different atoms.

The term "$C_1$-alkyl," as used herein, means methyl.

The term "$C_2$-alkyl," as used herein, means ethyl.

The term "$C_3$-alkyl," as used herein, means prop-1-yl and prop-2-yl(isopropyl).

The term "$C_4$-alkyl," as used herein, means but-1-yl, but-2-yl, 2-methylprop-1-yl and 2-methylprop-2-yl(tert-butyl).

The term "$C_5$-alkyl," as used herein, means 2,2-dimethylprop-1-yl(neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkylene," as used herein, means ethyl-1,2-ene, the ends of which are attached to different atoms.

The term "$C_3$-alkylene," as used herein, means propyl-1,3-ene, the ends of which are attached to different atoms.

The term "$C_4$-alkylene," as used herein, means butyl-1,4-ene, the ends of which are attached to different atoms.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_7$-cycloalkane," as used herein, means cycloheptane.

The term "$C_8$-cycloalkane," as used herein, means cyclooctane.

The term "$C_9$-cycloalkane," as used herein, means cyclononane.

The term "$C_{10}$-cycloalkane," as used herein, means cyclodecane.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_9$-cycloalkene," as used herein, means cyclononene, 1,3-cyclononadiene, 1,4-cyclononadiene, 1,5-cyclononadiene, 1,3,5-cyclononatriene, 1,3,6-cyclononatriene, 1,3,7-cyclononatriene and 1,3,5,7-cyclononatetraene.

The term "$C_{10}$-cycloalkene," as used herein, means cyclodecene, 1,3-cyclodecadiene, 1,4-cyclodecadiene, 1,5-cyclodecadiene, 1,6-cyclodecadiene, 1,3,5-cyclodecatriene, 1,3,6-cyclodecatriene, 1,3,5,7-cyclodecatetraene, 1,3,5,8-cyclodecatetraene and 1,3,6,8-cyclodecatetraene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "$C_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cyclooctal,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "$C_9$-cycloalkenyl," as used herein, means cyclonon-1-en-1-yl, cyclonon-2-en-1-yl, cyclonon-3-en-1-yl, cyclonon-4-en-1-yl, cyclonon-5-en-1-yl, cyclonona-1,3-dien-1-yl, cyclonona-1,4-dien-1-yl, cyclonona-1,5-dien-1-yl, cyclonona-1,6-dien-1-yl, cyclonona-1,7-dien-1-yl, cyclonona-1,8-dien-1-yl, cyclonona-2,4-dien-1-yl, cyclonona-2,5-dien-1-yl, cyclonona-2,6-dien-1-yl, cyclonona-2,7-dien-1-yl, cyclonona-2,8-dien-1-yl, cyclonona-3,5-dien-1-yl, cyclonona-3,6-dien-1-yl, cyclonona-3,7-dien-1-yl, cyclonona-4,6-dien-1-yl, cyclonona-1,3,5-trien-1-yl, cyclonona-1,3,6-trien-1-yl, cyclonona-1,3,7-trien-1-yl, cyclonona-1,3,8-trien-1-yl, cyclonona-1,4,6-trien-1-yl, cyclonona-1,4,7-trien-1-yl, cyclonona-1,4,8-trien-1-yl, cyclonona-1,5,7-trien-1-yl, cyclonona-1,5,8-trien-1-yl, cyclonona-1,6,8-trien-1-yl, cyclonona-2,4,8-trien-1-yl, cyclonona-2,4,6-trien-1-yl, cyclonona-2,4,7-trien-1-yl, cyclonona-2,4,8-trien-1-yl, cyclonona-2,5,7-trien-1-yl, cyclonona-2,5,8-trien-1-yl, cyclonona-1,3,5,7-tetraen-1-yl, cyclonona-1,3,5,8-tetraen-1-yl, cyclonona-1,3,6,8-tetraen-1-yl, cyclonona-1,4,6,8-tetraen-1-yl and cyclonona-2,4,6,8-tetraen-1-yl.

The term "$C_{10}$-cycloalkenyl," as used herein, means cyclodec-1-en-1-yl, cyclodec-2-en-1-yl, cyclodec-3-en-1-yl, cyclodec-4-en-1-yl, cyclodec-5-en-1-yl, cyclodeca-1,3-dien-1-yl, cyclodeca-1,4-dien-1-yl, cyclodeca-1,5-dien-1-yl, cyclodeca-1,6-dien-1-yl, cyclodeca-1,7-dien-1-yl, cyclodeca-1,8-dien-1-yl, cyclodeca-1,9-dien-1-yl, cyclodeca-2,4-dien-1-yl, cyclodeca-2,5-dien-1-yl, cyclodeca-2,6-dien-1-yl, cyclodeca-2,7-dien-1-yl, cyclodeca-2,8-dien-1-yl, cyclodeca-2,9-dien-1-yl, cyclodeca-3,5-dien-1-yl, cyclodeca-3,6-dien-1-yl, cyclodeca-3,7-dien-1-yl, cyclodeca-3,8-dien-1-yl, cyclodeca-4,6-dien-1-yl, cyclodeca-4,7-dien-1-yl, cyclodeca-1,3,5-trien-1-yl, cyclodeca-1,3,6-trien-1-yl, cyclodeca-1,3,7-trien-1-yl, cyclodeca-1,3,8-trien-1-yl, cyclodeca-1,3,9-trien-1-yl, cyclodeca-1,4,6-trien-1-yl, cyclodeca-1,4,7-trien-1-yl, cyclodeca-1,4,8-trien-1-yl, cyclodeca-1,4,9-trien-1-yl, cyclodeca-1,5,7-trien-1-yl, cyclodeca-1,5,8-trien-1-yl, cyclodeca-1,5,9-trien-1-yl, cyclodeca-1,6,8-trien-1-yl, cyclodeca-1,6,9-trien-1-yl, cyclodeca-1,7,9-trien-1-yl, cyclodeca-2,4,6-trien-1-yl, cyclodeca-2,4,7-trien-1-yl, cyclodeca-2,4,8-trien-1-yl, cyclodeca-2,4,9-trien-1-yl, cyclodeca-2,5,7-trien-1-yl, cyclodeca-2,5,8-trien-1-yl, cyclodeca-2,5,9-trien-1-yl, cyclodeca-2,6,8-trien-1-yl, cyclodeca-3,5,7-trien-1-yl, cyclodeca-3,5,8-trien-1-yl, cyclodeca-1,3,5,7-tetraen-1-yl, cyclodeca-1,3,5,8-tetraen-1-yl, cyclodeca-1,3,5,9-tetraen-1-yl, cyclodeca-1,3,6,8-tetraen-1-yl, cyclodeca-1,3,6,9-tetraen-1-yl, cyclodeca-1,3,7,9-tetraen-1-yl, cyclodeca-1,4,6,8-tetraen-1-yl, cyclodeca-1,4,6,9-tetraen-1-yl, cyclodeca-1,4,7,9-tetraen-1-yl, cyclodeca-1,5,7,9-tetraen-1-yl, cyclodeca-2,4,6,8-tetraen-1-yl, cyclodeca-2,4,6,9-tetraen-1-yl, cyclodeca-2,4,7,9-tetraen-1-yl and cyclodeca-1,3,5,7,9-pentaen-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "$C_7$-cycloalkyl," as used herein, means bicyclo[2.2.1]hept-1-yl, bicyclo[2.2.1]hept-2-yl, bicyclo[2.2.1]hept-7-yl and cyclohept-1-yl.

The term "$C_8$-cycloalkyl," as used herein, means bicyclo[2.2.2]oct-1-yl, bicyclo[2.2.2]oct-2-yl, bicyclo[2.2.2]oct-7-yl, cyclooct-1-yl.

The term "$C_9$-cycloalkyl," as used herein, means cyclonon-1-yl.

The term "$C_{10}$-cycloalkyl," as used herein, means adamant-1-yl, adamant-2-yl, cyclodec-1-yl and cyclodec-1-yl.

The term "perhaloalkenyl," as used herein, means $C_2$-perhaloalkenyl, $C_3$-perhaloalkenyl, $C_4$-perhaloalkenyl, $C_5$-perhaloalkenyl and $C_6$-perhaloalkenyl.

The term "$C_2$-perhaloalkenyl," as used herein, means $C_2$-alkenyl, each of the hydrogen atoms thereof having been replaced by independently selected F, Cl or Br atoms.

The term "$C_3$-perhaloalkenyl," as used herein, means $C_3$-alkenyl, each of the hydrogen atoms thereof having been replaced by independently selected F, Cl or Br atoms.

The term "$C_4$-perhaloalkenyl," as used herein, means $C_4$-alkenyl, each of the hydrogen atoms thereof having been replaced by independently selected F, Cl or Br atoms.

The term "$C_5$-perhaloalkenyl," as used herein, means $C_5$-alkenyl, each of the hydrogen atoms thereof having been replaced by independently selected F, Cl or Br atoms.

The term "$C_6$-perhaloalkenyl," as used herein, means $C_6$-alkenyl, each of the hydrogen atoms thereof having been replaced by independently selected F, Cl or Br atoms.

The term "perhaloalkyl," as used herein, means $C_1$-perhaloalkyl, $C_2$-perhaloalkyl, $C_3$-perhaloalkyl, $C_4$-perhaloalkyl, $C_5$-perhaloalkyl and $C_6$-perhaloalkyl.

The term "$C_1$-perhaloalkyl," as used herein, means $C_1$-alkyl, each of the hydrogen atoms thereof having been replaced by independently selected F, Cl or Br atoms.

The term "$C_2$-perhaloalkyl," as used herein, means $C_2$-alkyl, each of the hydrogen atoms thereof having been replaced by independently selected F, Cl or Br atoms.

The term "$C_3$-perhaloalkyl," as used herein, means $C_3$-alkyl, each of the hydrogen atoms thereof having been replaced by independently selected F, Cl or Br atoms.

The term "$C_4$-perhaloalkyl," as used herein, means $C_4$-alkyl, each of the hydrogen atoms thereof having been replaced by independently selected F, Cl or Br atoms.

The term "$C_5$-perhaloalkyl," as used herein, means $C_5$-alkyl, each of the hydrogen atoms thereof having been replaced by independently selected F, Cl or Br atoms.

The term "$C_6$-perhaloalkyl," as used herein, means $C_6$-alkyl, each of the hydrogen atoms thereof having been replaced by independently selected F, Cl or Br atoms.

The term "perhaloalkynyl," as used herein, means $C_2$-perhaloalkynyl, $C_3$-perhaloalkynyl, $C_4$-perhaloalkynyl, $C_5$-perhaloalkynyl and $C_6$-perhaloalkynyl.

The term "$C_2$-perhaloalkynyl," as used herein, means $C_2$-alkynyl, each of the hydrogen atoms thereof having been replaced by independently selected F, Cl or Br atoms.

The term "$C_3$-perhaloalkynyl," as used herein, means $C_3$-alkynyl, each of the hydrogen atoms thereof having been replaced by independently selected F, Cl or Br atoms.

The term "$C_4$-perhaloalkynyl," as used herein, means $C_4$-alkynyl, each of the hydrogen atoms thereof having been replaced by independently selected F, Cl or Br atoms.

The term "$C_5$-perhaloalkynyl," as used herein, means $C_5$-alkynyl, each of the hydrogen atoms thereof having been replaced by independently selected F, Cl or Br atoms.

The term "$C_6$-perhaloalkenyl," as used herein, means $C_6$-alkynyl, each of the hydrogen atoms thereof having been replaced by independently selected F, Cl or Br atoms.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds having formula (I) may have attached thereto prodrug-forming moieties which may be removed by metabolic processes to release the compounds having formula (I) in vivo. Prodrugs are useful for adjusting solubility, hydrophobicity, absorption, bioavailability, tissue penetration and rate of clearance of a compound.

Metabolites of compounds having formula (I), produced by in vitro or in vivo metabolic processes, may also have utility for treating diseases caused or exacerbated by the activity of anti-apoptotic Mcl-1 protein.

Certain precursor compounds of compounds having formula (I) may be metabolized in vitro or in vivo to form compounds having formula (I) and may thereby also have utility for treating diseases caused or exacerbated by the activity of anti-apoptotic Mcl-1 protein.

Compounds having formula (I) may exist as acid addition salts, basic addition salts or zwitterions. Salts of compounds having formula (I) are prepared during their isolation or following their purification. Acid addition salts are those derived from the reaction of the compounds having formula (I) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (I) are meant to be embraced by this invention. Basic addition salts of compounds are those derived from the reaction of the compounds having formula (I) with the bicarbonate, carbonate, hydroxide, or phosphate of cations such as lithium, sodium, potassium, calcium and magnesium.

Compounds having formula (I) may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Compounds having formula (I) may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having formula (I) to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having formula (I) to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having formula (I) to be administered osmotically include, for example, chlorofluorohydrocarbons, ethanol, water and mixtures thereof. Excipients for preparation of compositions comprising a compound having formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having formula (I) to be administered rectally or vaginally include, for example, cocoa butter, polyethylene glycol, wax and mixtures thereof.

(Fam)-NoxaCF (6-FAM)-GELEVEFATQLRRFGD-KLNF-amide) was made on a 433A automated synthesizer (Applied Biosystems, Foster City, Calif.) using standard Fastmoc™ deprotection/coupling cycles with 0.25 mmol MBHA Rink amide resin (SynPep, Dublin, Calif.). Cartridges containing $N^\alpha$-Fmoc-amino acids (1 mmol) with side-chain protection (Arg: 2,2,5,7,8-pentamethylchroman-6-sulfonyl; Asp and Glu: tert-butyl ester; Asn, Cys, Gln, and His: trityl; Lys and Trp: tert-butyloxycarbonyl; Ser, Thr, and Tyr: tert-butyl ether were activated with O-benzotriazol-1-yl-N,N,N',N'-tetramethyluronium hexafluorophosphate (1 mmol), 1-hydroxybenzotriazole (1 mmol) and diisopropylethylamine (2 mmol) in N-methylpyrrolidone (NMP). The activated amino acid was coupled for 30 minutes following removal of the N-terminal Fmoc group with 20% piperidine in NMP. Labeling was accomplished by suspending the resin-bound, N-terminally deprotected side-chain protected peptide resin (0.04 mmol) and 6-carboxyfluorescein-NHS ester (57 mg) in anhydrous dimethylformamide (2 mL) containing 0.02 mL diisopropylethylamine (DIEA) and shaking at ambient temperature overnight. The resin was drained, washed 3 times with 1:1 dichloromethane/methanol and dried. The labeled resin was cleaved and deprotected by mixing with TFA:water:thioanisole:phenol: 3,6-dioxa-1,8-octanedithiol:triisopropylsilane, 80:5:5:5:2.5:2.5 for 3 hours at ambient temperature. Following evaporation under reduced pressure, the crude peptide was recovered by precipitation with ether. The product was purified on a preparative HPLC running Unipoint® analysis software (Gilson, Inc., Middleton, Wis.) on a 25 mm×200 mm radial compression column containing Delta-Pak® $C_{18}$ packing (Waters, Inc., Taunton, Mass.) with a flow rate of 20 mL/min. The peptides were eluted with a linear gradient of 0.1% TFA/water and acetonitrile. Fractions containing the product were combined and lyophilized. The purity of the final products were confirmed by reverse-phase analytical HPLC on a Hewlett-Packard 1050 series system with diode-array and fluorescence detection (Agilent Technologies, Palo Alto, Calif.) eluted with a linear gradient of 0.1% trifluoroacetic acid/water and acetonitrile on a 4.6×250 mm YMC ODS-AQ, 5 µm, 120 Å column (Waters Inc.) to give the product (45.6 mg) as a yellow powder following lyophilization. The identity of the product was confirmed by matrix-assisted laser desorption ionization mass spectrography (MALDI-MS) on a Voyager DE-PRO (Applied Biosystems), m/z 1470.00 and 1448.01 (M+H)$^+$.

A fluorescence polarization assay was used for $IC_{50}$ determination of representative compounds having formula (I) against recombinant Mcl-1 protein. Compounds were series diluted in DMSO starting at 10 µM and transferred (5 µL) into a 96 well plate. Then, 120 µL of a mixture containing 10 nM fluorescent Noxa BH3 peptide and 80 nM Mcl-1 protein was added to each well. For each assay, free peptide controls (fluorescent peptide only) and bound peptide controls (fluorescent peptide in the presence of Mcl-1) were included on each assay plate. The plate was mixed on a shaker for 1 minute and incubated at room temperature for an additional 15 minutes. The polarization (in mP) was measured at room temperature with excitation wavelength at 485 nm and emission wavelength at 530 nm using an Analyst (LJL, Molecular Dynamic, Sunnyvale, Calif.). The percentage inhibition was calculated by % inhibition=$100\times(1-(mP-mP_f)/(mP_b-mP_f))$ in which $mP_f$ is the free peptide control and $mP_b$ is the bound peptide control. Based on percentage of inhibition, the $IC_{50}$ (inhibitor concentration at which 50% of bound peptide is displaced), obtained by fitting the inhibition data using Prism 3.0 software (Graphpad Software Inc, San Diego, Calif.), were 0.1 nM, 0.1 nM, 0.10 nM, 0.10 nM, 0.10 nM, 0.10 nM, 0.10 nM, 0.10 nM, 0.10 nM, 0.11 nM, 0.14 nM, 0.18 nM, 0.19 nM, 0.20 nM, 0.21 nM, 0.22 nM, 0.23 nM, 0.23 nM, 0.26 nM, 0.28 nM, 0.29 nM, 0.30 nM, 0.41 nM, 0.457 nM, 0.47 nM, 0.49 nM, 0.50 nM, 0.50 nM, 0.55 nM, 0.63 nM, 0.64 nM, 0.64 nM, 0.71 nM, 0.78 nM, 0.87 nM, 0.89 nM, 0.96 nM, 1.0 nM, 1.01 nM, 1.12 nM, 1.13 nM, 1.17 nM, 1.54 nM, 1.56 nM, 1.57 nM, 2.21 nM, 2.28 nM, 2.52 nM, 2.79 nM, 3.61 nM, 3.65 nM, 4.03 nM, 4.04 nM, 5 nM, 5.16 nM, 5.42 nM, 5.7 nM, 6.84 nM, 7.79 nM, 9.16 nM, 9.4 nM, 10 nM, 10.0 nM, >10 nM, >10 nM, >10 nM, >10 nM, >10 nM, >10 nM and >10 nM.

These data demonstrate the utility of compounds having formula (I) as binders to and inhibitors of anti-apoptotic Mcl-1 protein.

Accordingly, compounds having formula (I) are expected to have utility in treatment of diseases during which anti-apoptotic Mcl-1 is expressed.

It is expected that, because compounds having formula (I) bind to and inhibit the activity of Mcl-1, they would also have utility as inhibitors of anti-apoptotic family protein members having close structural homology to Mcl-1 such as, for example, Bcl-$X_L$ protein, Bcl-2 protein and Bcl-w protein.

Diseases during which Mcl-1 is expressed include, but are not limited to bladder cancer, brain cancer, breast cancer, cervical cancer, chronic lymphocytic leukemia, colorectal cancer, esophageal cancer, gastric cancer, glioblastoma, gestational trophobalstic disease, head and neck cancer, hepatocellular cancer, lymphoblastic leukemia, follicular lymphoma, lymphoid malignancies of T-cell or B-cell origin, melanoma, mesothioloma, multiple myeloma, myelogenous leukemia, myeloma, oral cancer, ovarian cancer, non-Hodgkin's lymphoma, non-small cell lung cancer, oligodenroglioma, pancreatic cancer, peripheral T-cell lymphoma, prostate cancer and small cell lung cancer.

Overexpression of Mcl-1 correlates with resistance to chemotherapy, clinical outcome, disease progression, overall prognosis or a combination thereof in various hematologic and solid tumor types.

Overexpression of Mcl-1 in acute lymphoblastic leukemia is reported in Blood 1998, 91, 991-1000.

Overexpression of Mcl-1 in acute myelogenous leukemia is also reported in Blood 1998, 91, 991-1000.

Overexpression of Mcl-1 in cervical cancer is reported in Cancer Letters (Shannon, Ireland) 2002, 180, 63-68.

Overexpression of Mcl-1 in chronic lymphocytic leukemia is reported in Journal of the National Cancer Institute 2004, 96, 673-682 and Immunology 2005, 114, 441-449.

Overexpression of Mcl-1 in colorectal cancer, is reported in Annals of oncology: Official Journal of the European Society for Medical Oncology/ESMO 2001, 12, 779-785.

Overexpression of Mcl-1 in gastric carcinoma, is reported in Gastric Cancer 2004, 7, 78-84.

Overexpression of Mcl-1 in gestational trophobalstic disease is reported in Cancer 2005, 103, 268-276.

Overexpression of Mcl-1 in glioblastoma is reported in Journal of Neurology, Neurosurgery, and Psychiatry 1999, 67, 763-768.

Overexpression of Mcl-1 in head and neck cancer is reported in Archives of Otolaryngology-Head and Neck Surgery 1999, 125, 417-422.

Overexpression of Mcl-1 in lung cancer is reported in Pathology Oncology Research: POR 1999, 5, 179-186.

Overexpression of Mcl-1 in mesothioloma, is reported in Clinical Cancer Research 1999, 5, 3508-3515.

Overexpression of Mcl-1 in multiple myeloma is reported in European Journal of Immunology 2004, 34, 3156-3164.

Overexpression of Mcl-1 in non-Hodgkin's lymphoma is reported in British Journal of Haematology 2002, 116, 158-161.

Overexpression of Mcl-1 in oligodenroglioma is reported in Cancer (New York) 1999, 86, 1832-1839.

Overexpression of Mcl-1 in ovarian cancer is reported in Journal of Clinical Oncology: Official Journal of the American Society of Clinical Oncology 2000, 18, 3775-3781.

Overexpression of Mcl-1 in pancreatic cancer is reported in Oncology 2002, 62, 354-362.

Overexpression of Mcl-1 in peripheral T-cell lymphoma is reported in Journal of Pathology 2003, 200, 240-248.

Compounds having formula (I) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl and triphenylmethyl.

Protecting groups for C(O) and C(O)H moieties include, but are not limited to, 1,3-dioxylketal, diethylketal, dimethylketal, 1,3-dithianylketal, O-methyloxime and O-phenyloxime.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl and 2-(triphenylphosphonio)ethoxycarbonyl.

A thorough discussion of protecting groups is provided in T. H. Greene and P. G. M. Wuts, Protective Groups in Organic Synthesis, 3$^{rd}$ Ed., John Wiley & Sons, New York (1999).

The following abbreviations have the meanings indicated. ADDP means 1,1'-(azodicarbonyl)dipiperidine; 9-BBN means 9-borabicyclo[3.3.1]nonane; (DHQD)$_2$PHAL means hydroquinidine 1,4-phthalazinediyl diethyl ether; DBU means 1,8-diazabicyclo[5.4.0]undec-7-ene; DEAD means diethyldiazocarboxylate; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporus triethylammonium methylpolystyrene cyanoborohydride; PyBOP means benzotriazol-1-yloxytripyrrolidinophosphonium hexafluorophosphate; TEA means triethylamine; TFA means trifluoroacetic acid; THF means tetrahydrofuran; NCS means N-chlorosuccinimide; NMM means N-methylmorpholine; NMP means N-methylpyrrolidine; PCh$_3$ means tricyclohexylphosphine; and PPh$_3$ means triphenylphosphine.

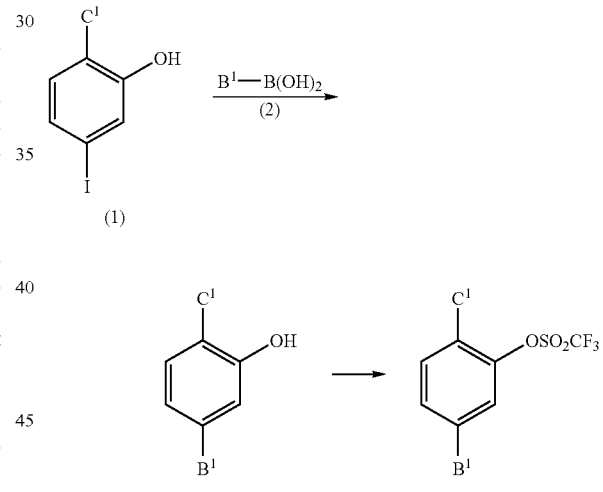

SCHEME 1

Compounds having formula (1) may be prepared as described in commonly-owned U.S. patent application Ser. No. 10/988,338.

Compounds having formula (1) may be converted to compounds having formula (3) by reacting the former, a compound having formula (2), tetrakis(triphenylphosphine)palladium(0) and cesium fluoride. The reaction is typically conducted at temperatures of about 50° C. to about 110° C. in solvents such as DME, THF, ethyl acetate or mixtures thereof.

Compounds having formula (3) may be converted to compounds having formula (4) by reacting the former, triflic anhydride and DIEA. The reaction is typically conducted at temperatures of about 0° C. to about 25° C. in solvents such as DME, THF, dichloromethane, ethyl acetate or mixtures thereof.

SCHEME 2

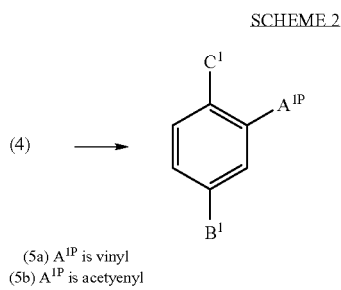

(5a) $A^{IP}$ is vinyl
(5b) $A^{IP}$ is acetyenyl

Compounds having formula (4) may be converted to compounds having formula (5a) by reacting the former, vinyltributyltin, LiCl and $PdCl_2(PPh_3)_2$. The reaction is typically conducted at temperatures of about 75° C. to about 100° C. in solvents such as THF, dioxane or mixtures thereof.

Compounds having formula (4) may be converted to compounds having formula (5b) by reacting the former, trimethylsilylacetylene, CuI and $PdCl_2(PPh_3)_2$. The reaction is typically conducted at temperatures of about 60° C. to about 100° C. in solvents such as THF, DMF, dioxane or mixtures thereof.

SCHEME 3

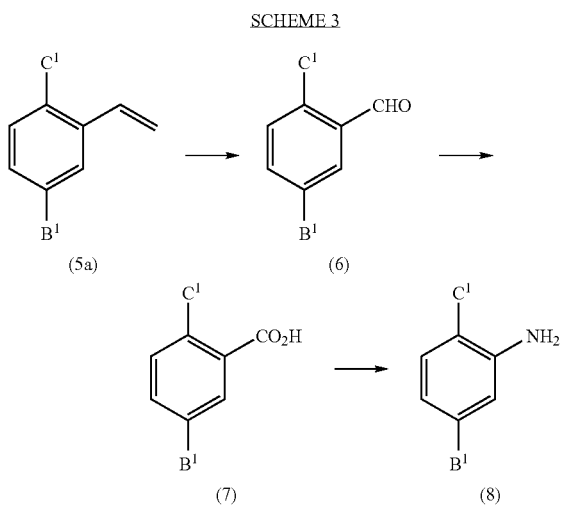

Compounds having formula (5a) may be converted to compounds having formula (6) by reacting the former and $RuO_4$. The reaction is typically conducted at temperatures of about 60° C. to about 100° C. in solvents such as THF, dioxane or mixtures thereof.

Compounds having formula (6) may be converted to compounds having formula (7) by reacting the former and aqueous $H_2O_2$; and compounds having formula (7) may be converted to compounds having formula (8) by reacting the former and DPPA and TEA. Conversion of compounds having formula (6) to compounds having formula (7) is typically conducted at temperatures of about 0° C. to about 30° C. in solvents such as THF, dioxane, water, or mixtures thereof, and conversion of compounds having formula (7) to compounds having formula (8) is typically conducted at temperatures of about 75° C. to about 110° C. in solvents such as benzene or toluene.

Compounds having formula (8) may also be prepared by reducing the corresponding nitro-containing compound with hydrogen and palladium on carbon in methanol, ethanol, isopropanol or a mixture thereof at temperatures of about 50° C. to about 110° C.

Compounds having formulas (3) and (6)-(8) may be converted to compounds having formula (I) by the appropriate coupling reaction, examples of which are shown in the following examples which are presented to provide what is believed to be the most useful and readily understood description of procedures and conceptual aspects of this invention.

EXAMPLE 1A

Methyl 4-chloro-2-methoxybenzoate (6.5 g), 4-fluorobenzeneboronic acid (4.5 g), CsF (12.5 g) and $PdCl_2(PCh_3)_2$ (750 mg) in NMP (65 mL) at 90° C. were stirred for 24 hours, cooled, diluted with ethyl acetate, and washed with water and brine. The extract was dried ($Na_2SO_4$), filtered and concentrated. The concentrate was chromatographed on silica gel with 10% ethyl acetate/hexanes.

EXAMPLE 1B

EXAMPLE 1A (6.37 g) in dichloromethane (100 mL) at −78° C. was treated with 1M $BBr_3$ dichloromethane (40 mL), stirred for 2 hours, quenched with methanol (20 mL) and partitioned between ethyl acetate and water. The extract was dried ($Na_2SO_4$), filtered and concentrated.

EXAMPLE 1C

EXAMPLE 1B (500 mg), trifluoromethanesulfonic anhydride (0.42 mL) and TEA (0.43 mL) in dichloromethane (5 mL) at 0° C. were stirred for 5 hours, diluted with dichloromethane, washed with water and brine and dried ($Na_2SO_4$), filtered and concentrated.

EXAMPLE 1D

EXAMPLE 1C (378 mg), vinyltributyltin (380 mg), LiCl (128 mg), and $PdCl_2(PPh_3)_2$ (35 mg) in dioxane (3 mL) at 100° C. were stirred for 2 hours, cooled, diluted with diethyl ether, treated with DBU (0.2 mL) and water (3 drops), stirred for 30 minutes, filtered through silica gel (20 g), and concentrated. The concentrate was chromatographed on silica gel with 5% ethyl acetate/hexanes.

EXAMPLE 1E

EXAMPLE 1D (1.05 g), 3-bromobiphenyl (1.05 g), $PdCl_2(PPh_3)_2$ (50 mg) and TEA (0.5 mL) in DMF (10 mL) at 60° C. were stirred for 24 hours, cooled, poured into ether, washed with water and brine and concentrated. The concentrate was chromatographed on silica gel with 5% ethyl acetate/hexane.

EXAMPLE 1F

EXAMPLE 1E (690 mg) and $LiOH.H_2O$ (290 mg) in THF (5 mL), methanol (2 mL) and water (2 mL) at ambient temperature were stirred for 24 hours, acidified with concentrated HCl and extracted with diethyl ether. The extract was washed with brine and concentrated. $^1H$ NMR (300 MHz, DMSO-$d_6$) δ 8.11 (d, 1H), 8.09 (d, 1H), 7.98 (d, 1H), 7.90 (dd, 2H), 7.86 (d, 1H), 7.72 (d, 2H), 7.68 (dd, 1H), 7.61 (m, 2H), 7.51 (m, 3H), 7.42 (m, 2H), 7.36 (dd, 2H).

EXAMPLE 2

This example was made by substituting EXAMPLE 1F for EXAMPLE 47D in EXAMPLE 47E. $^1H$ NMR (300 MHz, CD$_3$OD) δ 8.01 (d, 1H), 7.54 (m, 5H), 7.39 (m, 5H), 7.32 (dd, 2H), 7.19 (d, 1H), 7.13 (dd, 2H), 3.38 (m, 2H), 3.01 (t, 2H).

EXAMPLE 3A

This example was made by substituting 2-bromobiphenyl for 3-bromobiphenyl in EXAMPLE 1E.

EXAMPLE 3B

This example was made by substituting EXAMPLE 3A for EXAMPLE 1E in EXAMPLE 1F. $^1$H NMR (300 MHz, CD$_3$OD) δ 8.00 (d, 1H), 7.96 (d, 1H), 7.81 (d, 1H), 7.60 (dd, 2H), 7.55 (dd, 1H), 7.42 (m, 7H), 7.35 (m, 2H), 7.19 (dd, 2H), 7.01 (d, 1H).

EXAMPLE 4A

This example was made by substituting 3-iodoaniline for 3-bromobiphenyl in EXAMPLE 1E.

EXAMPLE 4B

EXAMPLE 4A (86 mg), 4-trifluoromethylbenzenesulfonyl chloride (120 mg), DMAP (10 mg) and TEA (0.13 mL) in dichloromethane (5 mL) were stirred at ambient temperature for 24 hours, filtered through silica gel and chromatographed on silica gel with 5% ethyl acetate/hexane.

EXAMPLE 4C

This example was made by substituting EXAMPLE 4B for EXAMPLE 1E in EXAMPLE 1F. $^1$H NMR (300 MHz, DMSO-d$_6$) δ 7.98 (m, 6H), 7.86 (m, 4H), 7.64 (dd, 1H), 7.47 (d, 2H), 7.34 (dd, 2H), 7.24 (d, 1H), 7.14 (d, 2H).

EXAMPLE 5A

This example was made by substituting EXAMPLE 4B for EXAMPLE 47D in EXAMPLE 47E.

EXAMPLE 5B

This example was made by substituting EXAMPLE 5A for EXAMPLE 1E in EXAMPLE 1F. $^1$H NMR (300 MHz, CDCl$_3$) δ 8.19 (d, 1H), 7.86 (m, 3H), 7.69 (d, 12H), 7.60 (dd, 2H), 7.47 (m, 2H), 7.17 (m, 4H), 7.00 (d, 2H), 3.31 (t, 2H), 2.90 (t, 2H).

EXAMPLE 6A

This example was made by substituting 8-amino-2-naphthol for EXAMPLE 1B in EXAMPLE 1C.

EXAMPLE 6B

This example was made by substituting EXAMPLE 6A for 3-bromobiphenyl in EXAMPLE 1E.

EXAMPLE 6C

This example was made by substituting EXAMPLE 6B for EXAMPLE 1B in EXAMPLE 1C.

EXAMPLE 6D

This example was made by substituting EXAMPLE 6C for EXAMPLE 1E in EXAMPLE 1F. $^1$H NMR (300 MHz, CD$_3$OD) δ 8.30 (d, 1H), 8.26 (d, 1H), 8.06 (dd, 2H), 7.93 (dd, 2H), 7.87 (dd, 1H), 7.79 (dd, 2H), 7.63 (dd, 1H), 7.54 (dd, 1H), 7.48 (m, 1H), 7.39 (d, 1H), 7.25 (dd, 2H).

EXAMPLE 7

This example was made by substituting EXAMPLE 6B for EXAMPLE 1E in EXAMPLE 1F. $^1$H NMR (300 MHz, CD$_3$OD) δ 8.19 (d, 1H), 8.07 (d, 2H), 8.04 (d, 1H), 7.77 (m, 4H), 7.59 (dd, 1H), 7.38 (d, 1H), 7.24 (m, 4H), 6.84 (m, 1H).

EXAMPLE 8A

This example was made by substituting 2-benzylbromobenzene for 3-bromobiphenyl in EXAMPLE 1E.

EXAMPLE 8B

This example was made by substituting EXAMPLE 8A for EXAMPLE 1E in EXAMPLE 1F.

EXAMPLE 8C

This example was made by substituting EXAMPLE 8B for EXAMPLE 47D in EXAMPLE 47E. $^1$H NMR (300 MHz, CD$_3$OD) δ 7.96 (d, 1H), 7.50 (m, 3H), 7.22 (m, 1H), 7.18 (m, 8H), 7.10 (m, 2H), 7.02 (d, 1H), 3.97 (s, 2H), 3.13 (t, 2H), 2.88 (t, 2H).

EXAMPLE 9A

This example was made by substituting 4-bromobenzylphenol for 3-bromobiphenyl in EXAMPLE 1E.

EXAMPLE 9B

This example was made by substituting EXAMPLE 9A for EXAMPLE 1E in EXAMPLE 1F. $^1$H NMR (300 MHz, CD$_3$OD) δ 8.11 (d, 1H), 8.00 (m, 2H), 7.77 (dd, 2H), 7.60 (m, 3H), 7.45 (d, 2H), 7.23 (m, 4H), 7.19 (d, 1H), 6.99 (d, 2H), 6.91 (dd, 1H), 5.09 (s, 2H).

EXAMPLE 10A

This example was made by substituting 4-bromophenyl phenyl ether for 3-bromobiphenyl in EXAMPLE 1E.

EXAMPLE 10B

This example was made by substituting EXAMPLE 10A for EXAMPLE 1E in EXAMPLE 1F. $^1$H NMR (300 MHz, CD$_3$OD) δ 8.03 (d, 1H), 7.98 (m, 2H), 7.75 (dd, 2H), 7.57 (m, 3H), 7.36 (m, 3H), 7.22 (m, 2H), 7.11 (m, 3H), 6.99 (d, 2H).

EXAMPLE 11A

Naphthalene-2,7-diol (1.60 g) and DIEA (1.74 mL) in dichloromethane (10 mL) at −78° C. were treated with TBSOTf (2.3 mL), warmed to ambient temperature over 30 minutes, treated with DIEA (1.74 mL), cooled to −78° C., treated with triflic anhydride (2 mL), warmed to ambient temperature over 30 minutes and partitioned between water and diethyl ether. The extract was dried (MgSO$_4$), filtered and concentrated. The concentrate was chromatographed on silica gel with 5% ethyl acetate/hexanes.

EXAMPLE 11B

This example was made by substituting EXAMPLE 11A for 3-bromobiphenyl in EXAMPLE 1E.

EXAMPLE 11C

This example was made by substituting EXAMPLE 11B for EXAMPLE 47C in EXAMPLE 47D.

EXAMPLE 11D

This example was made by substituting EXAMPLE 11C for EXAMPLE 1E in EXAMPLE 1F. $^1$H NMR (300 MHz, CD$_3$OD) δ 8.19 (d, 1H), 8.03 (m, 2H), 7.79 (dd, 2H), 7.75 (d, 1H), 7.70 (m, 2H), 7.59 (m, 2H), 7.33 (d, 1H), 7.24 (dd, 2H), 7.11 (dd, 1H), 7.04 (dd, 1H).

EXAMPLE 12A

This example was made by substituting naphthalene-2,6-diol for naphthalene-2,7-diol in EXAMPLE 11A.

EXAMPLE 12B

This example was made by substituting EXAMPLE 12A for EXAMPLE 11A in EXAMPLE 11B.

EXAMPLE 12C

This example was made by substituting EXAMPLE 12B for EXAMPLE 11B in EXAMPLE 11C.

EXAMPLE 12D

EXAMPLE 12C (20 mg), Ph$_3$P (52 mg) and cyclohexylmethanol (23 mg) in dichloromethane (2 mL) at 0° C. was treated with DEAD (0.032 mL), warmed to ambient temperature, stirred for 24 hours and chromatographed on silica gel with 5% ethyl acetate/hexanes.

EXAMPLE 12E

This example was made by substituting EXAMPLE 12D for EXAMPLE 1E in EXAMPLE 1F. $^1$H NMR (300 MHz, CDCl$_3$) δ 8.20 (d, 1H), 8.17 (d, 1H), 7.95 (d, 1H), 7.76 (d, 1H), 7.72 (m, 5H), 7.53 (d, 1H), 7.20 (m, 3H), 7.14 (m, 2H), 3.88 (d, 2H), 1.91 (m, 1H), 1.77 (m, 2H), 1.22 (m, 4H), 1.12 (m, 2H).

EXAMPLE 13A

This example was made by substituting 4-benzylbromobenzene for 3-bromobiphenyl in EXAMPLE 1E.

EXAMPLE 13B

This example was made by substituting EXAMPLE 13A for EXAMPLE 1E in EXAMPLE 1F. $^1$H NMR (300 MHz, DMSO-d$_6$) δ 8.02 (d, 1H), 7.91 (m, 3H), 7.63 (dd, 1H), 7.50 (d, 2H), 7.34 (d, 2H), 7.25 (m, 8H), 7.21 (m, 1H), 3.96 (s, 2H).

EXAMPLE 14A

This example was made by substituting 4-bromo-4'-n-propylbiphenyl for 3-bromobiphenyl in EXAMPLE 1E.

EXAMPLE 14B

This example was made by substituting EXAMPLE 14A for EXAMPLE 1E in EXAMPLE 1F. $^1$H NMR (300 MHz, CD$_3$OD) δ 8.12 (d, 1H), 8.01 (m, 2H), 7.77 (dd, 2H), 7.63 (d, 2H), 7.57 (m, 4H), 7.24 (m, 6H), 2.63 (t, 2H), 1.67 (tq, 1H), 0.97 (t, 3H).

EXAMPLE 15A

EXAMPLE 1C (5.20 g), trimethylsilylacetylene (2.9 mL), PdCl$_2$(PPh$_3$)$_2$ (480 mg), CuI (390 mg), tetrabutylammonium iodide (1.52 g) and TEA (20 mL) in DMF (60 mL) were stirred at 70° C. for 40 minutes, cooled, diluted with ethyl acetate, washed with water and dried (MgSO$_4$), filtered and concentrated. The concentrate was dissolved in acetonitrile (100 mL) and water (2 mL), treated with KF (1.17 g), stirred for 1 hour and concentrated. The concentrate was chromatographed on silica gel with 20% ethyl acetate/hexanes.

EXAMPLE 15B

EXAMPLE 15A (500 mg), 4-iodoaniline (950 mg), PdCl$_2$dppf (236 mg), CuI (20 mg), and pyrrolidine (6 mL) in DMF (3 mL) were stirred at ambient temperature for 24 hours and concentrated. The concentrate was diluted with ethyl acetate, washed with water and dried (MgSO$_4$), filtered and concentrated. The concentrate was chromatographed on silica gel with 30% ethyl acetate/hexanes.

EXAMPLE 15C

EXAMPLE 15B (40 mg), 4-trifluoromethylbenzaldehyde (0.02 mL), sodium triacetoxyborohydride (40 mg), Na$_2$SO$_4$ (70 mg) and acetic acid (0.030 mL) in 1,2-dichloroethane (2 mL) were stirred at ambient temperature for 24 hours and chromatographed on silica gel with 30% ethyl acetate/hexanes.

EXAMPLE 15D

This example was made by substituting EXAMPLE 15C for EXAMPLE 1E in EXAMPLE 1F. $^1$H NMR (300 MHz, DMSO-d$_6$) δ 7.94 (d, 1H), 7.81 (m, 3H), 7.70 (m, 3H), 7.59 (d, 2H), 7.33 (dd, 2H), 7.25 (d, 2H), 6.93 (t, 1H), 6.61 (d, 2H), 4.44 (d, 2H).

EXAMPLE 16A

EXAMPLE 15B (60 mg), 2-quinonoyl chloride (0.052 mL) and TEA (0.050 mL), in dichloromethane (2 mL) were stirred at ambient temperature for 24 hours and chromatographed on silica gel with 5% ethyl acetate/hexanes.

EXAMPLE 16B

This example was made by substituting EXAMPLE 16A for EXAMPLE 1E in EXAMPLE 1F. $^1$H NMR (300 MHz, DMSO-d$_6$) δ 11.07 (s, 1H), 9.57 (s, 1H), 8.33 (m, 1H), 8.23 (m, 1H), 8.06 (m, 5H), 7.96 (m, 2H), 7.86 (m, 2H), 7.80 (m, 2H), 7.61 (d, 2H), 7.35 (dd, 2H).

EXAMPLE 17A

This example was made by substituting 4-iodoaniline for 3-bromobiphenyl in EXAMPLE 1E.

EXAMPLE 17B

This example was made by substituting EXAMPLE 17A for EXAMPLE 15B in EXAMPLE 15C.

EXAMPLE 17C

This example was made by substituting EXAMPLE 17B for EXAMPLE 1E in EXAMPLE 1F. $^1$H NMR (300 MHz, DMSO-d$_6$) δ 8.01 (d, 1H), 7.99 (d, 1H), 7.87 (d, 2H), 7.81 (dd, 1H), 7.68 (m, 2H), 7.59 (m, 4H), 7.51 (d, 1H), 7.32 (d, 2H), 6.87 (dd, 1H), 6.62 (d, 2H), 4.42 (m, 1H), 4.32 (d, 2H).

EXAMPLE 18A

This example was made by substituting 2-naphthoyl chloride for 2-quinonoyl chloride in EXAMPLE 16A.

EXAMPLE 18B

This example was made by substituting EXAMPLE 18A for EXAMPLE 1E in EXAMPLE 1F. $^1$H NMR (300 MHz, DMSO-d$_6$) δ 10.53 (s, 1H), 8.61 (§, 1H), 8.11 (d, 1H), 8.05 (m, 4H), 7.86 (m, 4H), 7.77 (dd, 2H), 7.64 (m, 4H), 7.53 (d, 2H), 7.39 (d, 1H), 7.29 (dd 2H).

EXAMPLE 19A

4-Chloro-2-nitrobenzoic acid methyl ester (862 mg), 4-fluorophenylboronic acid (611 mg) and PdCl$_2$(PPh$_3$)$_2$ (84 mg) in toluene (20 mL) and 2M Na$_2$CO$_3$ (5 mL) at 100° C. were stirred for 24 hours and cooled. The layers were separated, and the extract was concentrated. The concentrate was chromatographed on silica gel with 10% ethyl acetate/hexanes.

EXAMPLE 19B

EXAMPLE 19A (980 mg) and 10% Pd/C (1 g) in methanol (10 mL) under hydrogen at 50° C. were stirred for 1 hour, cooled and filtered through diatomaceous earth (Celite®).

EXAMPLE 19C

EXAMPLE 19B (75 mg) and TEA (0.21 mL) in dichloromethane (2 mL) were treated with 3-trifluoromethylbenzenesulfonyl chloride (90 mg), stirred at ambient temperature for 24 hours and partitioned between dichloromethane and water. The extract was dried (Na$_2$SO$_4$), filtered and concentrated.

EXAMPLE 19D

This example was made by substituting EXAMPLE 19C for EXAMPLE 1E in EXAMPLE 1F. $^1$H NMR (300 MHz, CD$_3$OD) δ 8.06 (m, 2H), 8.00 (d, 1H), 7.82 (m, 2H), 7.67 (m, 1H), 7.59 (dd, 2H), 7.29 (m, 1H), 7.20 (m, 2H).

EXAMPLE 20A

This example was made by substituting trans-styrene sulfonyl chloride for 3-trifluoromethylbenzenesulfonyl chloride in EXAMPLE 19C.

EXAMPLE 20B

This example was made by substituting EXAMPLE 20A for EXAMPLE 1E in EXAMPLE 1F. $^1$H NMR (300 MHz, CD$_3$OD) δ 8.08 (m, 1H), 7.81 (s, 1H), 7.60 (m, 3H), 7.52 (m, 2H), 7.37 (m, 3H), 7.29 (m, 1H), 7.18 (dd, 2H), 7.05 (d, 1H).

EXAMPLE 21A

This example was made by substituting 4-methylbenzenesulfonyl chloride for 3-trifluoromethylbenzenesulfonyl chloride in EXAMPLE 19C.

EXAMPLE 21B

This example was made by substituting EXAMPLE 21A for EXAMPLE 1E in EXAMPLE 1F. $^1$H NMR (300 MHz, CD$_3$OD) δ 7.99 (m, 1H), 7.78 (d, 1H), 7.70 (d, 2H), 7.57 (dd, 2H), 7.23 (m, 3H), 7.19 (m, 2H), 2.31 (s, 3H).

EXAMPLE 22A

This example was made by substituting 4-vinylbenzenesulfonyl chloride for 3-trifluoromethylbenzenesulfonyl chloride in EXAMPLE 19C.

EXAMPLE 22B

This example was made by substituting EXAMPLE 22A for EXAMPLE 1E in EXAMPLE 1F. $^1$H NMR (300 MHz, CD$_3$OD) δ 8.03 (m, 1H), 7.79 (m, 3H), 7.57 (m, 2H), 7.41 (m, 2H), 7.18 (m, 3H), 6.62 (dd, 1H), 5.77 (d, 1H), 5.29 (d, 1H).

EXAMPLE 23A

This example was made by substituting 4-trifluoromethylbenzenesulfonyl chloride for 3-trifluoromethylbenzenesulfonyl chloride in EXAMPLE 19C.

EXAMPLE 23B

This example was made by substituting EXAMPLE 23A for EXAMPLE 1E in EXAMPLE 1F. $^1$H NMR (300 MHz, CD$_3$OD) δ 8.01 (d, 1H), 7.87 (d, 2H), 7.74 (d, 1H), 7.60 (m, 3H), 7.15 (m, 2H), 6.95 (d, 1H), 6.80 (dd, 1H).

EXAMPLE 24A

This example was made by substituting 5-dimethylamino-2-naphthylsulfonyl chloride for 3-trifluoromethylbenzenesulfonyl chloride in EXAMPLE 19C.

EXAMPLE 24B

This example was made by substituting EXAMPLE 23A for EXAMPLE 1E in EXAMPLE 1F. $^1$H NMR (300 MHz, CD$_3$OD) δ 8.48 (d, 1H), 8.39 (dd, 2H), 7.92 (d, 1H), 7.61 (s, 1H), 7.53 (m, 2H), 7.45 (m, 2H), 7.14 (m, 3H), 7.04 (d, 1H), 2.77 (s, 6H).

EXAMPLE 25A

This example was made by substituting 4-(dimethylamino) azobenzyl-4-sulfonyl chloride for 3-trifluoromethylbenzenesulfonyl chloride in EXAMPLE 19C.

EXAMPLE 25B

This example was made by substituting EXAMPLE 25A for EXAMPLE 1E in EXAMPLE 1F. $^1$H NMR (300 MHz, CD$_3$OD) δ 8.00 (d, 1H), 7.90 (dd, 2H), 7.80 (m, 5H), 7.63 (dd, 2H), 7.29 (d, 1H), 7.22 (dd, 2H), 6.80 (d, 2H), 3.10 (s, 6H).

EXAMPLE 26A

This example was made by substituting 2-(4-pyridyl)ethylsulfonyl chloride for 3-trifluoromethylbenzenesulfonyl chloride in EXAMPLE 19C.

EXAMPLE 26B

This example was made by substituting EXAMPLE 26A for EXAMPLE 1E in EXAMPLE 1F. $^1$H NMR (300 MHz, CD$_3$OD) δ 8.34 (m, 2H), 8.14 (d, 1H), 7.82 (s, 1H), 7.64 (dd, 2H), 7.35 (d, 1H), 7.20 (m, 4H), 3.51 (t, 2H), 3.12 (t, 2H).

EXAMPLE 27A

This example was made by substituting 2-thiophenesulfonyl chloride for 3-trifluoromethylbenzenesulfonyl chloride in EXAMPLE 19C.

EXAMPLE 27B

This example was made by substituting EXAMPLE 27A for EXAMPLE 1E in EXAMPLE 1F. $^1$H NMR (300 MHz, CD$_3$OD) δ 8.04 (d, 1H), 7.87 (d, 1H), 7.64 (m, 2H), 7.61 (dd, 2H), 7.24 (d, 1H), 7.20 (dd, 2H), 7.01 (dd, 1H).

EXAMPLE 28A

EXAMPLE 202034B (151 mg) in THF (5 mL) at −78° C. was treated with lithium bis(trimethylsilyl)amide (1M, 1.5 mL), stirred for 30 minutes, treated with 4-chloro-3-nitrobenzenesulfonyl chloride (174 mg), stirred at ambient temperature for 4 hours, poured into water and extracted with ethyl acetate. The extract was washed with NaHCO$_3$ solution, water and brine and dried (Na$_2$SO$_4$), filtered and concentrated. The concentrate was chromatographed on silica gel with 20% ethyl acetate/hexanes.

EXAMPLE 28B

EXAMPLE 28A (50 mg) and cyclohexylpropylamine (30 mg) in dioxane (5 mL) at 50° C. were stirred for 24 hours, cooled and chromatographed on silica gel with 20% ethyl acetate/hexanes.

EXAMPLE 28C

This example was made by substituting EXAMPLE 28B for EXAMPLE 1E in EXAMPLE 1F. $^1$H NMR (300 MHz, DMSO-d$_6$) δ 8.51 (t, 1H), 8.47 (s, 1H), 7.93 (d, 1H), 7.77 (dd, 1H), 7.66 (m, 3H), 7.33 (m, 3H), 7.15 (d, 1H), 3.45 (m, 2H), 1.61 (m, 7H), 1.19 (m, 6H), 0.82 (m, 2H).

EXAMPLE 29A

This example was made by substituting 2-(phenylthio)ethylamine for cyclohexylpropylamine in EXAMPLE 28B.

EXAMPLE 29B

This example was made by substituting EXAMPLE 29A for EXAMPLE 1E in EXAMPLE 1F. $^1$H NMR (400 MHz, DMSO-d$_6$) δ 8.65 (t, 1H), 8.43 (s, 1H), 7.95 (d, 1H), 7.72 (d, 1H), 7.64 (m, 3H), 7.33 (m, 5H), 7.18 (dd, 2H), 7.11 (m, 2H), 3.60 (dt, 2H), 3.23 (t, 2H).

EXAMPLE 30A

2-Chloroethylamine hydrochloride (1.4 g) in 3M NaOH (8 mL) at 80° C. were stirred for 50 minutes, cooled to 0° C., treated with diethyl ether (40 mL) and 4-chloro-3-nitrobenzenesulfonyl chloride (1.54 g) and stirred for 1 hour. The layers were separated and the extract was washed with water and dried (MgSO$_4$), filtered and concentrated.

EXAMPLE 30B

EXAMPLE 30A (100 mg) and EXAMPLE 19B (281 mg) in THF (3 mL) in a sealed vial were heated at 70° C. for 24 hours, cooled and chromatographed on silica gel with 15% ethyl acetate/hexanes.

EXAMPLE 30C

This example was made by substituting EXAMPLE 30B for EXAMPLE 1E in EXAMPLE 1F. $^1$H NMR (300 MHz, CDCl$_3$) δ 8.33 (s, 1H), 8.00 (d, 1H), 7.89 (d, 1H), 7.55 (m, 4H), 7.16 (dd, 2H), 6.90 (d, 1H), 6.81 (s, 1H), 6.82 (s, 1H), 3.50 (m, 2H), 3.42 (m, 2H).

EXAMPLE 31A

This example was made by substituting EXAMPLE 30B for EXAMPLE 28A and cyclohexylmethylamine for cyclohexylpropylamine in EXAMPLE 28B.

EXAMPLE 31B

This example was made by substituting EXAMPLE 31A for EXAMPLE 1E in EXAMPLE 1F. $^1$H NMR (300 MHz, DMSO-d$_6$) δ 8.47 (t, 1H), 8.29 (s, 1H), 7.82 (t, 1H), 7.74 (d, 1H), 7.67 (m, 3H), 7.29 (dd, 2H), 7.02 (d, 1H), 6.79 (s, 1H), 6.74 (d, 1H), 4.03 (s, 1H), 3.38 (m, 2H), 3.21 (t, 2H), 3.00 (m, 2H), 1.71 (m, 6H), 1.24 (m, 2H), 1.17 (m, 3H).

EXAMPLE 32A

This example was made by substituting EXAMPLE 30B for EXAMPLE 28A and cyclohexylethylamine for cyclohexylpropylamine in EXAMPLE 28B.

EXAMPLE 32B

This example was made by substituting EXAMPLE 32A for EXAMPLE 1E in EXAMPLE 1F. $^1$H NMR (300 MHz, DMSO-d$_6$) δ 8.39 (t, 1H), 8.28 (s, 1H), 7.83 (t, 1H), 7.73 (d, 1H), 7.67 (m, 3H), 7.29 (dd, 2H), 6.98 (d, 1H), 6.78 (s, 1H), 6.73 (d, 1H), 4.03 (s, 1H), 3.44 (m, 2H), 3.29 (t, 2H), 3.01 (m, 2H), 1.70 (m, 5H), 1.52 (m, 2H), 1.23 (m, 2H), 1.19 (m, 2H), 0.95 (m, 2H).

EXAMPLE 33A

EXAMPLE 19B (50 mg) and 4-chloro-3-nitrobenzaldehyde (93 mg) in THF (1 mL) were treated with titanium isopropoxide (0.18 mL), stirred for 24 hours, treated with NaBH$_4$ (50 mg), stirred at ambient temperature for 3 hours, poured into dichloromethane (20 mL), filtered through a plug of silica gel and concentrated. The concentrate was chromatographed on silica gel with 20% ethyl acetate/hexanes.

EXAMPLE 33B

This example was made by substituting EXAMPLE 33A for EXAMPLE 28A in EXAMPLE 28B.

EXAMPLE 33C

This example was made by substituting EXAMPLE 33B for EXAMPLE 1E in EXAMPLE 1F. $^1$H NMR (400 MHz, DMSO-d$_6$) δ 8.10 (m, 1H), 8.09 (s, 1H), 7.87 (d, 1H), 7.63 (dd, 2H), 7.56 (d, 12H), 7.24 (dd, 2H), 7.05 (d, 1H), 6.82 (s, 1H), 6.77 (d, 1H), 4.43 (s, 2H), 4.05 (s, 1H), 3.29 (m, 2H), 1.65 (m, 5H), 1.23 (m, 4H), 1.14 (m, 4H), 0.85 (m, 2H).

EXAMPLE 34A

7-Methoxy-1-tetralone (17.6 g) in 48% HBr solution (60 Ml) at reflux was stirred for 15 hours, cooled, poured into brine (90 mL) and extracted with ethyl acetate. The extract was washed with brine and concentrated. The concentrate was chromatographed on silica gel with 20% ethyl acetate/hexanes.

EXAMPLE 34B

This example was made by substituting EXAMPLE 34A for EXAMPLE 1B in EXAMPLE 1C.

EXAMPLE 34C

EXAMPLE 34B (4.81 g) and para-toluenesulfonic acid hydrate (400 mg) in 2-propenyl acetate (40 mL) were refluxed for 24 hours, treated with DDQ (9.6 g), stirred at 80° C. for 4 hours, poured into ethyl acetate, washed with Na$_2$CO$_3$ solution, water and brine and dried (MgSO$_4$), filtered and concentrated. The concentrate was chromatographed on silica gel with 40% ethyl acetate/hexanes.

EXAMPLE 34D

This example was made by substituting allyltributyltin for vinyltributyltin and EXAMPLE 34C for EXAMPLE 1C in EXAMPLE 1D.

EXAMPLE 34E

EXAMPLE 34D (2.26 g) and N-methylmorpholine-N-oxide (1.29 g) in THF (20 mL) and water (3 mL) were treated with 0.08M OsO$_4$ in THF (5 mL), stirred for 24 hours, treated with NaIO$_4$ (2.4 g) and water (10 mL), stirred for 1 hour, poured into ethyl acetate, washed with water and brine and dried (MgSO$_4$), filtered and concentrated. The concentrate was chromatographed on silica gel with 30% ethyl acetate/hexanes.

EXAMPLE 34F

EXAMPLE 34E (122 mg) and EXAMPLE 19B (140 mg) in 1,2-dichloroethane (5 mL) were treated with sodium triacetoxyborohydride (170 mg), stirred for 24 hours, treated with water (0.5 mL) and chromatographed on silica gel with 20% ethyl acetate/hexanes.

EXAMPLE 34G

This example was made by substituting EXAMPLE 34F EXAMPLE 1E in EXAMPLE 1F. $^1$H NMR (300 MHz, CD$_3$OD) δ 8.10 (s, 1H), 7.93 (d, 1H), 7.69 (d, 1H), 7.57 (dd, 2H), 7.40 (d, 1H), 7.23 (m, 3H), 7.12 (m, 2H), 6.87 (d, 1H), 6.78 (dd, 2H), 3.65 (t, 2H), 3.14 (t, 2H).

EXAMPLE 35A

2-Allylphenol (3.34 g), K$_2$CO$_3$ (6.87 g) and benzyl bromide (3.2 mL) in DMF (20 mL) were stirred at ambient temperature for 1 hour, poured into diethyl ether, washed with water and brine and dried (MgSO$_4$), filtered and concentrated. The concentrate was chromatographed on silica gel with 5% ethyl acetate/hexanes.

EXAMPLE 35B

EXAMPLE 35A (2.62 g) in THF (50 mL) at ambient was treated with 0.5M 9-BBN in THF (26 mL), stirred for 24 hours, added to 1:1 methanol/THF (50 mL) then 1:1 2M NaOH/30% H$_2$O$_2$ (100 mL), stirred for 3 hours and treated with NaCl. The two layers were separated, and the aqueous layer was extracted with diethyl ether. The extract was washed with 1M NaOH and brine and dried (MgSO$_4$), filtered, and concentrated. The concentrate was chromatographed on silica gel with 30% ethyl acetate/hexanes.

EXAMPLE 35C

EXAMPLE 35B (75 mg), EXAMPLE 1B (77 mg), ADDP (157 mg) and PBu$_3$ (0.156 mL) in benzene (10 mL) at ambient temperature were stirred for 24 hours and chromatographed on silica gel with 5% ethyl acetate/hexanes.

EXAMPLE 35D

This example was made by substituting EXAMPLE 35C for EXAMPLE 47D in EXAMPLE 47E.

EXAMPLE 35E

This example was made by substituting EXAMPLE 35D for EXAMPLE 1E in EXAMPLE 1F. $^1$H NMR (300 MHz, CDCl$_3$) δ 8.24 (d, 1H), 7.55 (dd, 2H), 7.30 (m, 1H), 7.14 (m, 5H), 6.88 (dd, 1H), 6.75 (m, 1H), 4.33 (t, 2H), 2.88 (t, 2H), 2.27 (m, 2H).

EXAMPLE 36A 5,6,7,8-tetrahydro-1-naphthol (2.96 g), Ph$_3$P (6.3 g), DEAD (3.8 mL) and 3-bromo-1-propanol (2.2 mL) in dichloromethane (50 mL) at 0° C. were stirred for 1 hour and at ambient temperature for 24 hours, filtered through silica gel and concentrated. The concentrate was chromatographed on silica gel with 10% ethyl acetate/hexanes.

EXAMPLE 36B

EXAMPLE 1B (100 mg) in DMF (5 mL) at 0° C. was treated with K$_2$CO$_3$ (50 mg) and 18-crown-6 (30 mg), stirred for 10 minutes, treated with EXAMPLE 36A (130 mg), stirred at ambient temperature for 1 hour, treated with one drop of water and chromatographed on silica gel with 10% ethyl acetate/hexanes.

EXAMPLE 36C

This example was made by substituting EXAMPLE 34F for EXAMPLE 1E in EXAMPLE 1F. $^1$H NMR (300 MHz, DMSO-d$_6$) δ 7.77 (m, 2H), 7.73 (d, 1H), 7.31 (m, 4H), 7.02 (dd, 1H), 6.74 (d, 1H), 6.64 (d, 1H), 4.34 (t, 2H), 4.16 (t, 2H), 2.66 (m, 2H), 2.55 (m, 2H), 2.20 (tt, 2H), 1.66 (m, 4H).

EXAMPLE 37A 2-(1-Naphthyl)ethanol (1.73 g) and Dess-Martin reagent (12.7 g) in dichloromethane (80 mL) at ambient temperature were stirred for 3 hours, filtered through a silica gel plug and concentrated. The concentrate was dissolved in THF (50 mL), treated with methyl(triphenylphosphoranylidene)acetate (4.01 g), stirred for 24 hours, diluted with hexane, filtered through a silica gel plug and concentrated.

EXAMPLE 37B

EXAMPLE 37A (100 mg) in dichloromethane (2 mL) at −78° C. was treated with 1M DIBAL in toluene (2 mL), stirred at ambient temperature for 2 hours, quenched with methanol, poured into 1M HCl (10 mL) and extracted with ethyl acetate. The extract was filtered through a plug of silica gel and concentrated.

EXAMPLE 37C

This example was made by substituting EXAMPLE 37B for 3-bromo-1-propanol and EXAMPLE 1B for 5,6,7,8-tetrahydro-1-naphthol in EXAMPLE 36A.

EXAMPLE 37D

This example was made by substituting EXAMPLE 37C for EXAMPLE 1E in EXAMPLE 1F. $^1$H NMR (300 MHz, DMSO-$d_6$) δ 8.07 (d, 1H), 7.90 (d, 1H), 7.81 (d, 1H), 7.69 (m, 3H), 7.51 (m, 2H), 7.37 (dd, 2H), 7.26 (m, 4H), 6.17 (m, 1H), 5.85 (m, 1H), 4.75 (d, 2H), 3.88 (d, 2H).

EXAMPLE 38A

4-Fluoro-3-nitrobenzoic acid (227 mg) in SOCl$_2$ (3 mL) at reflux was stirred for 3 hours, cooled and concentrated. The concentrate was dissolved in dichloromethane (10 mL), and this mixture was treated with EXAMPLE 19B (300 mg) and DIEA (1 mL), stirred at ambient temperature for 24 hours, poured into saturated NaHCO$_3$, and extracted with ethyl acetate. The extract was concentrated to 5 mL, filtered and concentrated.

EXAMPLE 38B

EXAMPLE 38A (40 mg) and 2-propylphenol (15 mg) in THF (2 mL) at ambient temperature were treated with 60% oily NaH (5 mg), stirred for 24 hours and chromatographed on silica gel with 20% ethyl acetate/hexanes.

EXAMPLE 38C

This example was made by substituting EXAMPLE 38B for EXAMPLE 1E in EXAMPLE 1F. $^1$H NMR (300 MHz, DMSO-$d_6$) δ 8.92 (d, 1H), 8.63 (d, 1H), 8.18 (dd, 1H), 8.14 (d, 1H), 7.77 (dd, 2H), 7.53 (d, 1H), 7.38 (m, 6H), 7.17 (d, 1H), 7.07 (d, 2H), 2.53 (t, 2H), 1.56 (m, 2H), 0.86 (t, 3H).

EXAMPLE 39A

EXAMPLE 38A (30 mg) and cyclohexylmethylamine (0.1 mL) in THF (1.5 mL) at ambient temperature were stirred for 5 minutes and concentrated. The concentrate was dissolved in THF/ethyl acetate, filtered through silica gel and concentrated.

EXAMPLE 39B

This example was made by substituting EXAMPLE 39A for EXAMPLE 1E in EXAMPLE 1F. $^1$H NMR (300 MHz, DMSO-$d_6$) δ 9.02 (d, 1H), 8.77 (d, 1H), 8.57 (t, 1H), 8.10 (d, 1H), 8.06 (d, 1H), 7.77 (dd, 2H), 7.49 (d, 1H), 7.37 (dd, 2H), 7.28 (d, 1H), 3.22 (m, 2H), 1.72 (m, 6H), 1.18 (m, 3H), 1.01 (m, 2H).

EXAMPLE 40A

This example was made by substituting 1-adamantylmethylamine for cyclohexylmethylamine in EXAMPLE 39A.

EXAMPLE 40B

This example was made by substituting EXAMPLE 40A for EXAMPLE 1E in EXAMPLE 1F. $^1$H NMR (300 MHz, DMSO-$d_6$) δ 9.02 (d, 1H), 8.79 (d, 1H), 8.54 (t, 1H), 8.12 (d, 1H), 8.06 (d, 1H), 7.77 (dd, 2H), 7.49 (d, 1H), 7.38 (dd, 2H), 7.35 (d, 1H), 3.22 (m, 2H), 1.99 (s, 3H), 1.64 (m, 6H), 1.60 (s, 6H).

EXAMPLE 41A

This example was made by substituting 2-(phenylthio)ethylamine for cyclohexylmethylamine in EXAMPLE 39A.

EXAMPLE 41B

This example was made by substituting EXAMPLE 41A for EXAMPLE 1E in EXAMPLE 1F. $^1$H NMR (300 MHz, DMSO-$d_6$) δ 9.02 (d, 1H), 8.75 (d, 1H), 8.72 (t, 1H), 8.11 (d, 1H), 8.02 (d, 1H), 7.77 (dd, 2H), 7.50 (d, 1H), 7.38 (m, 5H), 7.32 (dd, 2H), 7.22 (d, 1H), 3.68 (dt, 2H), 3.22 (t, 2H).

EXAMPLE 42A

This example was made by substituting 2-(cyclohexylthio)ethylamine for cyclohexylmethylamine in EXAMPLE 39A.

EXAMPLE 42B

This example was made by substituting EXAMPLE 42A for EXAMPLE 1E in EXAMPLE 1F. $^1$H NMR (300 MHz, DMSO-$d_6$) δ 9.02 (d, 1H), 8.79 (d, 1H), 8.71 (t, 1H), 8.12 (d, 1H), 8.08 (d, 1H), 7.77 (dd, 2H), 7.49 (d, 1H), 7.38 (dd, 2H), 7.30 (d, 1H), 3.64 (dt, 2H), 2.85 (t, 2H), 2.65 (m, 1H), 1.95 (m, 2H), 1.69 (m, 2H), 1.26 (m, 6H).

EXAMPLE 43A

4-Bromophthalic anhydride (250 mg) in methanol (10 mL) at ambient temperature was treated with SOCl$_2$ (0.5 mL), stirred for 24 hours and concentrated with a toluene azeotrope.

EXAMPLE 43B

This example was made by substituting EXAMPLE 43A for 4-chloro-2-methoxybenzoic acid methyl ester in EXAMPLE 1A.

EXAMPLE 43C

This example was made by substituting EXAMPLE 43B for EXAMPLE 1E in EXAMPLE 1F.

EXAMPLE 43D

EXAMPLE 43C (760 mg), 4-fluoro-3-nitroaniline (502 mg), EDCI (611 mg), and HOBt (432 mg) in DMF (10 mL) at ambient temperature were stirred for 24 hours, diluted with dichloromethane, washed with water and concentrated. The concentrate was dissolved in DMF (3 mL), treated with dichloromethane and filtered.

EXAMPLE 43E

EXAMPLE 43D (30 mg) in THF (1 mL) was treated with 2-(phenylthio)ethylamine (0.2 mL), stirred at 50° C. for 8 hours, treated with ethyl acetate, washed with 1M HCl (10 mL) and concentrated. The concentrate was chromatographed on silica gel with 5% methanol/dichloromethane. $^1$H NMR (300 MHz, DMSO-$d_6$) δ 8.61 (d, 1H), 8.28 (t, 1H), 7.94 (d, 1H), 7.84 (m, 4H), 7.71 (dd, 1H), 7.40 (dd, 2H), 7.35 (m, 4H), 7.23 (d, 1H), 7.04 (d, 1H), 4.03 (s, 1H), 3.58 (dt, 2H), 3.28 (t, 2H).

EXAMPLE 44A

This example was made by substituting 1-adamantylmethylamine for 2-(phenylthio)ethylamine in EXAMPLE 43E. $^1$H NMR (300 MHz, DMSO-$d_6$) δ 8.70 (d, 1H), 8.22 (t, 1H), 8.08 (d, 1H), 7.75 (m, 3H), 7.70 (dd, 2H), 7.31 (dd, 2H), 7.20 (d, 1H), 3.12 (m, 2H), 1.94 (s, 3H), 1.65 (m, 6H), 1.59 (s, 6H).

EXAMPLE 45A

This example was made by substituting cyclohexylmethylamine for 2-(phenylthio)ethylamine in EXAMPLE 43E. $^1$H NMR (300 MHz, DMSO-$d_6$) δ 8.68 (d, 1H), 8.16 (t, 1H), 7.96 (d, 1H), 7.77 (m, 5H), 7.33 (dd, 2H), 7.11 (d, 1H), 4.03 (s, 1H), 3.22 (t, 2H), 1.74 (m, 6H), 1.21 (m, 3H), 1.02 (m, 2H).

EXAMPLE 46A

Example 1D (564 mg) in water (6 mL), $CH_3CN$ (4 mL) and $CCl_4$ (4 mL) at ambient temperature was treated with $RuCl_3.H_2O$ (24 mg) and $NaIO_4$ (2.48 g), stirred for 2 hours, and poured into water (50 mL) and extracted with dichloromethane. The extract was washed with brine and dried ($Na_2SO_4$), filtered and concentrated.

EXAMPLE 46B

EXAMPLE 46A (40 mg), 6-amino-1-naphthol (80 mg), EDCI (100 mg) and DMAP (10 mg) in DMF (1 mL) at ambient temperature were stirred for 24 hours, diluted with ethyl acetate (20 mL), washed with water and brine and concentrated. The concentrate was chromatographed on silica gel with 30% ethyl acetate/hexanes.

EXAMPLE 46C

This example was made by substituting EXAMPLE 46B for EXAMPLE 1E in EXAMPLE 1F. $^1$H NMR (300 MHz, $CD_3OD$) δ 8.27 (m, 1H), 8.14 (d, 1H), 8.01 (d, 1H), 7.89 (d, 1H), 7.82 (d, 1H), 7.74 (m, 3H), 7.60 (dd, 1H), 7.25 (d, 2H), 7.21 (dd, 2H), 6.74 (dd, 1H).

EXAMPLE 47A

6-Bromo-2-naphthol (4.46 g) and DIEA (4.5 mL) in dichloromethane (50 mL) at ambient temperature were treated with TBSOTf (5.05 mL), stirred for 24 hours, diluted with ethyl acetate (200 mL), washed with water and brine and concentrated. The concentrate was chromatographed on silica gel with 5% ethyl acetate/hexanes.

EXAMPLE 47B

EXAMPLE 47A (337 mg), allyltributyltin (400 mg), and $Pd(PPh_3)_4$ (78 mg) in toluene (5 mL) at 100° C. were stirred for 24 hours, cooled and chromatographed on silica gel with 5% ethyl acetate/hexanes.

EXAMPLE 47C

EXAMPLE 47B (243 mg), EXAMPLE 1C (151 mg), $PdCl_2dppf$ (50 mg) and TEA (0.5 mL) in DMF (2 mL) at 100° C. were stirred for 24 hours, cooled, poured into diethyl ether, washed with water and brine and concentrated. The concentrate was chromatographed on silica gel with 2% ethyl acetate/hexanes.

EXAMPLE 47D

EXAMPLE 47C (243 mg) and 1M TBAF in THF (0.5 mL) in THF (2 mL) at ambient temperature were stirred for 3 hours, filtered through a silica gel plug and concentrated. The concentrate was chromatographed on silica gel with 20% ethyl acetate/hexanes.

EXAMPLE 47E

EXAMPLE 47D (19 mg) and 10% Pd/C (20 mg) in ethyl acetate (2 mL) at ambient temperature were stirred for 3 hours, filtered through a plug of diatomaceous earth (Celite®) then silica gel and concentrated. The concentrate was chromatographed on silica gel with 20% ethyl acetate/hexanes.

EXAMPLE 47F

This example was made by substituting EXAMPLE 47A for EXAMPLE 1E in EXAMPLE 1F. $^1$H NMR (300 MHz, $CDCl_3$) δ 8.10 (d, 1H), 7.64 (d, 1H), 7.59 (m, 3H), 7.44 (m, 2H), 7.28 (m, 1H), 7.14 (m, 5H), 3.18 (t, 2H), 2.86 (t, 2H), 1.93 (m, 2H).

EXAMPLE 48A

EXAMPLE 47A (675 mg), 1M 4-butenylmagnesium bromide in THF (3 mL) and $Pd(PPh_3)_4$ (75 mg) in THF (5 mL) at reflux were stirred for 24 hours, cooled, filtered through a silica gel plug and concentrated. The concentrate was chromatographed on silica gel with 5% ethyl acetate/hexanes.

EXAMPLE 48B

This example was made by substituting EXAMPLE 48A for EXAMPLE 47B in EXAMPLE 47C.

EXAMPLE 48C

This example was made by substituting EXAMPLE 48B for EXAMPLE 47C in EXAMPLE 47D.

EXAMPLE 48D

This example was made by substituting EXAMPLE 48C for EXAMPLE 1E in EXAMPLE 1F. $^1$H NMR (300 MHz, $CDCl_3$) δ 8.07 (d, 1H), 7.66 (m, 1H), 7.60 (m, 3H), 7.53 (m, 3H), 7.29 (m, 1H), 7.13 (m, 5H), 6.25 (m, 1H), 2.97 (t, 2H), 2.89 (dt, 2H).

EXAMPLE 49A

This example was made by substituting EXAMPLE 48C for EXAMPLE 47D in EXAMPLE 47E.

EXAMPLE 49B

This example was made by substituting EXAMPLE 49A for EXAMPLE 1E in EXAMPLE 1F. $^1$H NMR (300 MHz, CDCl$_3$) δ 8.07 (d, 1H), 7.69 (d, 1H), 7.64 (m, 3H), 7.46 (m, 2H), 7.32 (m, 5H), 7.18 (m, 1H), 3.25 (t, 2H), 2.64 (t, 2H), 1.57 (m, 4H).

EXAMPLE 50A

Magnesium (292 mg) in THF (19 mL) at ambient temperature was treated with 4-pentenylbromide (1.49 g), stirred for 1 hour, treated with EXAMPLE 47A (675 mg) and PdCl$_2$(PPh$_3$)$_2$ (75 mg), stirred at reflux for 2 hours, cooled, filtered through a silica gel plug, and concentrated. The concentrate was chromatographed on silica gel with 5% ethyl acetate/hexanes.

EXAMPLE 50B

This example was made by substituting EXAMPLE 50A for EXAMPLE 47B in EXAMPLE 47C.

EXAMPLE 50C

This example was made by substituting EXAMPLE 50B for EXAMPLE 47C in EXAMPLE 47D.

EXAMPLE 50D-1, AND EXAMPLE 50D-2

These compounds were made by substituting EXAMPLE 50C for EXAMPLE 47D in EXAMPLE 47E.

EXAMPLE 50E

This example was made by substituting EXAMPLE 50D1 for EXAMPLE 1E in EXAMPLE 1F. $^1$H NMR (300 MHz, CDCl$_3$) δ 8.07 (d, 1H), 7.56 (m, 3H), 7.48 (m, 3H), 7.29 (m, 1H), 7.14 (m, 5H), 3.07 (t, 2H), 2.74 (m, 2H), 1.74 (m, 2H), 1.59 (m, 4H).

EXAMPLE 51

This example was made by substituting EXAMPLE 50D2 for EXAMPLE 1E in EXAMPLE 1F. $^1$H NMR (300 MHz, CDCl$_3$) δ 8.14 (d, 1H), 7.56 (dd, 2H), 7.42 (m, 1H), 7.32 (m, 3H), 7.21 (m, 2H), 7.07 (dd, 1H), 3.88 (m, 1H), 3.75 (m, 1H), 3.41 (t, 2H), 3.01 (t, 2H), 2.95 (m, 4H), 1.94 (m, 2H), 1.25 (m, 4H), 0.88 (tt, 2H).

EXAMPLE 52A

This example was made by substituting 7-methoxynaphthol for EXAMPLE 1B in EXAMPLE 1C.

EXAMPLE 52B

This example was made by substituting EXAMPLE 52A for EXAMPLE 47A in EXAMPLE 47B.

EXAMPLE 52C

This example was made by substituting EXAMPLE 52B for EXAMPLE 47B in EXAMPLE 47C.

EXAMPLE 52D

This example was made by substituting EXAMPLE 52C for EXAMPLE 1E in EXAMPLE 1F. $^1$H NMR (300 MHz, CDCl$_3$) δ 8.08 (d, 1H), 7.77 (d, 1H), 7.67 (m, 1H), 7.57 (m, 2H), 7.52 (m, 2H), 7.36 (m, 1H), 7.14 (m, 6H), 6.32 (m, 1H), 3.25 (t, 2H), 2.76 (dt, 2H).

EXAMPLE 53A

This example was made by substituting EXAMPLE 52C for EXAMPLE 1A in EXAMPLE 1B.

EXAMPLE 53B

This example was made by substituting EXAMPLE 53A for EXAMPLE 1E in EXAMPLE 1F. $^1$H NMR (300 MHz, CDCl$_3$) δ 8.10 (d, 1H), 7.79 (d, 1H), 7.68 (m, 1H), 7.60 (m, 2H), 7.50 (m, 2H), 7.32 (m, 1H), 7.17 (m, 6H), 6.34 (m, 1H), 3.17 (t, 2H), 2.66 (dt, 2H).

EXAMPLE 54A

This example was made by substituting EXAMPLE 52C for EXAMPLE 47D in EXAMPLE 47E.

EXAMPLE 54B

This example was made by substituting EXAMPLE 54A for EXAMPLE 1E in EXAMPLE 1F. $^1$H NMR (300 MHz, CDCl$_3$) δ 8.10 (d, 1H), 7.74 (d, 1H), 7.61 (m, 1H), 7.58 (m, 2H), 7.43 (d, 2H), 7.29 (m, 1H), 7.14 (m, 5H), 3.91 (s, 3H), 3.16 (t, 2H), 3.08 (t, 2H), 1.84 (m, 4H).

EXAMPLE 55A

This example was made by substituting EXAMPLE 54A for EXAMPLE 1A in EXAMPLE 1B.

EXAMPLE 55B

This example was made by substituting EXAMPLE 55A for EXAMPLE 1E in EXAMPLE 1F. $^1$H NMR (300 MHz, CDCl$_3$) δ 8.11 (d, 1H), 7.94 (d, 1H), 7.55 (m, 3H), 7.43 (m, 2H), 7.33 (dd, 1H), 7.14 (m, 5H), 3.15 (t, 2H), 3.08 (t, 2H), 1.84 (m, 4H).

EXAMPLE 56A

This example was made by substituting 4-fluoro-3-nitro-1-bromobenzene for 3-bromobiphenyl in EXAMPLE 1E.

EXAMPLE 56B

EXAMPLE 56A (1 g) and cyclohexylpropylamine (500 mg) in dioxane (10 mL) at 60° C. was stirred for 12 hours, cooled and chromatographed on silica gel with 10% ethyl acetate/hexanes.

EXAMPLE 56C

EXAMPLE 56B (920 mg) and SnCl$_2$ (1.5 g) in ethyl acetate (20 mL) at reflux were stirred for 24 hours, cooled, filtered through silica gel and concentrated. The concentrate was chromatographed on silica gel with 25% ethyl acetate/hexanes.

EXAMPLE 56D

EXAMPLE 56C (100 mg), benzyl bromide (0.03 mL), and TEA (0.1 mL) in acetonitrile (2 mL) were refluxed for 2 hours, cooled and chromatographed on silica gel with 20% ethyl acetate/hexanes.

EXAMPLE 56E

This example was made by substituting EXAMPLE 56D for EXAMPLE 1E in EXAMPLE 1F. $^1$H NMR (300 MHz, CD$_3$OD) δ 7.98 (d, 1H), 7.88 (m, 2H), 7.78 (dd, 2H), 7.57 (d, 1H), 7.35 (m, 3H), 7.27 (m, 4H), 7.12 (m, 2H), 7.01 (dd, 2H), 4.55 (m, 1H), 4.09 (s, 2H), 2.94 (t, 2H), 1.71 (m, 5H), 1.95 (m, 2H), 2.06 (s, 1H), 1.21 (m, 5H), 1.17 (m, 2H).

EXAMPLE 57

This example was made by substituting EXAMPLE 56B for EXAMPLE 1E in EXAMPLE 1F. $^1$H NMR (300 MHz, DMSO-d$_6$) δ 8.324 (t, 1H), 8.25 (d, 1H), 8.07 (d, 1H), 7.91 (m, 4H), 7.81 (dd, 1H), 7.64 (dd, 1H), 7.35 (m, 3H), 7.16 (d, 1H), 3.40 (m, 2H), 1.68 (m, 7H), 1.27 (m, 4H), 1.16 (m, 2H), 0.88 (m, 2H).

EXAMPLE 58A

EXAMPLE 56C (500 mg) and NaNO$_2$ (90 mg) in concentrated HCl (2 mL) and acetone (10 mL) at ambient temperature were stirred for 24 hours, diluted with ethyl acetate, washed with NaHCO$_3$ solution and water and concentrated. The concentrate was chromatographed on silica gel with 25% ethyl acetate/hexanes.

EXAMPLE 58B

This example was made by substituting EXAMPLE 58A for EXAMPLE 1E in EXAMPLE 1F. $^1$H NMR (300 MHz, DMSO-d$_6$) δ 8.14 (d, 1H), 8.08 (d, 1H), 7.92 (m, 6H), 7.70 (d, 1H), 7.54 (d, 1H), 7.37 (dd, 2H), 4.70 (t, 2H), 1.92 (m, 2H), 1.61 (m, 5H), 1.15 (m, 6H), 0.81 (m, 2H).

EXAMPLE 59A

This example was made by substituting cyclohexylamine for cyclohexylpropylamine in EXAMPLE 56B.

EXAMPLE 59B

This example was made by substituting EXAMPLE 59A for EXAMPLE 1E in EXAMPLE 1F. $^1$H NMR (300 MHz, DMSO-d$_6$) δ 8.24 (d, 1H), 8.16 (d, 1H), 8.06 (d, 1H), 7.88 (m, 4H), 7.61 (d, 1H), 7.34 (m, 3H), 7.22 (d, 1H), 3.17 (d, 2H), 2.01 (m, 2H), 1.70 (m, 2H), 1.40 (m, 6H).

EXAMPLE 60A

EXAMPLE 56A (100 mg), thiophenol (37 mg), and K$_2$CO$_3$ (35 mg) in dioxane (2 mL) at 80° C. were stirred for 24 hours, cooled and chromatographed on silica gel with 10% ethyl acetate/hexanes.

EXAMPLE 60B

This example was made by substituting EXAMPLE 60A for EXAMPLE 1E in EXAMPLE 1F. $^1$H NMR (300 MHz, DMSO-d$_6$) δ 8.41 (d, 1H), 8.10 (d, 1H), 8.07 (d, 1H), 7.94 (d, 1H), 7.87 (dd, 2H), 7.82 (dd, 1H), 7.64 (m, 5H), 7.47 (d, 1H), 7.35 (dd, 2H), 6.99 (d, 1H).

EXAMPLE 61A

This example was made by substituting cyclohexylmethylamine for cyclohexylpropylamine in EXAMPLE 56B.

EXAMPLE 61B

This example was made by substituting EXAMPLE 61A for EXAMPLE 1E in EXAMPLE 1F. $^1$H NMR (300 MHz, DMSO-d$_6$) δ 8.35 (t, 1H), 8.22 (d, 1H), 8.02 (d, 1H), 7.92 (d, 1H), 7.85 (m, 4H), 7.57 (d, 1H), 7.37 (dd, 13H), 7.32 (m, 3H), 7.14 (d, 1H), 3.26 (m, 2H), 1.73 (m, 6H), 1.20 (m, 3H), 1.01 (m, 2H).

EXAMPLE 62A

This example was made by substituting piperidine for cyclohexylpropylamine in EXAMPLE 56B.

EXAMPLE 62B

This example was made by substituting EXAMPLE 62A for EXAMPLE 1E in EXAMPLE 1F. $^1$H NMR (300 MHz, DMSO-d$_6$) δ 8.04 (d, 1H), 7.96 (m, 2H), 7.88 (m, 3H), 7.77 (d, 1H), 7.65 (d, 1H), 7.34 (dd, 2H), 7.33 (dd, 2H), 3.01 (m, 4H), 1.61 (m, 6H).

EXAMPLE 63A

This example was made by substituting phenol for thiophenol in EXAMPLE 60A.

EXAMPLE 63B

This example was made by substituting EXAMPLE 63A for EXAMPLE 1E in EXAMPLE 1F. $^1$H NMR (300 MHz, CD$_3$OD) δ 8.15 (d, 1H), 8.11 (d, 1H), 7.99 (m, 2H), 7.84 (dd, 1H), 7.76 (dd, 2H), 7.61 (d, 1H), 7.42 (dd, 2H), 7.22 (m, 5H), 7.07 (m, 2H).

EXAMPLE 64A

This example was made by substituting 5,6,7,8-tetrahydro-1-naphthol for thiophenol in EXAMPLE 60A.

EXAMPLE 64B

This example was made by substituting EXAMPLE 64A for EXAMPLE 1E in EXAMPLE 1F. $^1$H NMR (300 MHz, CD$_3$OD) δ 8.13 (d, 1H), 8.04 (d, 1H), 7.99 (m, 2H), 7.78 (m, 3H), 7.62 (d, 1H), 7.22 (m, 4H), 6.96 (d, 1H), 6.87 (d, 1H), 6.76 (d, 1H), 2.83 (m, 2H), 2.65 (m, 2H), 1.80 (m, 4H).

EXAMPLE 65A

This example was made by substituting tryptamine for cyclohexylpropylamine in EXAMPLE 56B.

EXAMPLE 65B

This example was made by substituting EXAMPLE 314678A for EXAMPLE 1E in EXAMPLE 1F. $^1$H NMR (300 MHz, DMSO-d$_6$) δ 8.38 (t, 1H), 8.23 (d, 1H), 7.91 (d, 1H), 7.88 (m, 5H), 7.62 (d, 2H), 7.35 (m, 6H), 7.22 (d, 1H), 7.07 (dd, 1H), 6.99 (dd, 1H), 3.70 (dt, 2H), 3.10 (t, 2H).

EXAMPLE 66A

This example was made by substituting benzylphenethylamine for cyclohexylpropylamine in EXAMPLE 56B.

EXAMPLE 66B

This example was made by substituting EXAMPLE 66A for EXAMPLE 1E in EXAMPLE 1F. $^1$H NMR (300 MHz, DMSO-$d_6$) δ 8.02 (d, 1H), 7.92 (m, 3H), 7.88 (m, 2H), 7.67 (m, 2H), 7.31 (m, 8H), 7.23 (m, 4H), 7.12 (m, 2H), 4.47 (s, 2H), 3.27 (t, 2H), 2.79 (m, 2H).

EXAMPLE 67A

This example was made by substituting 2-(phenylthio)ethylamine for cyclohexylpropylamine in EXAMPLE 56B.

EXAMPLE 67B

This example was made by substituting EXAMPLE 67A for EXAMPLE 1E in EXAMPLE 1F. $^1$H NMR (300 MHz, DMSO-$d_6$) δ 8.51 (t, 1H), 8.24 (d, 1H), 8.06 (d, 1H), 7.88 (m, 4H), 7.80 (d, 1H), 7.61 (m, 1H), 7.41 (m, 2H), 7.34 (m, 5H), 7.23 (d, 1H), 7.11 (d, 1H), 3.64 (dt, 2H), 3.42 (t, 2H).

EXAMPLE 68A

This example was made by substituting 4-cyclopentylphenol for thiophenol in EXAMPLE 60A.

EXAMPLE 68B

This example was made by substituting EXAMPLE 68A for EXAMPLE 1E in EXAMPLE 1F. $^1$H NMR (300 MHz, CD$_3$OD) δ 8.13 (d, 1H), 8.05 (d, 1H), 7.99 (d, 1H), 7.78 (m, 4H), 7.62 (d, 1H), 7.29 (d, 1H), 7.22 (m, 3H), 7.01 (m, 4H), 3.03 (m, 1H), 2.06 (m, 2H), 1.84 (m, 2H), 1.72 (m, 2H), 1.60 (m, 2H).

EXAMPLE 69A

This example was made by substituting 3-tert-butylphenol for thiophenol in EXAMPLE 60A.

EXAMPLE 69B

This example was made by substituting EXAMPLE 69A for EXAMPLE 1E in EXAMPLE 1F. $^1$H NMR (300 MHz, CD$_3$OD) δ 8.14 (d, 1H), 8.06 (d, 1H), 7.97 (m, 2H), 7.82 (d, 1H), 7.75 (m, 2H), 7.60 (dd, 1H), 7.34 (m, 2H), 7.22 (m, 3H), 7.12 (d, 1H), 7.04 (d, 1H), 6.87 (dd, 1H), 1.32 (s, 9H).

EXAMPLE 70A

This example was made by substituting 2-morpholinophenol for thiophenol in EXAMPLE 60A.

EXAMPLE 70B

This example was made by substituting EXAMPLE 70A for EXAMPLE 1E in EXAMPLE 1F. $^1$H NMR (300 MHz, DMSO-$d_6$) δ 8.23 (d, 1H), 8.07 (m, 2H), 7.88 (m, 4H), 7.69 (m, 2H), 7.35 (m, 4H), 7.17 (m, 2H), 6.81 (d, 1H), 3.44 (m, 4H), 2.95 (m, 4H).

EXAMPLE 71A

This example was made by substituting 2-benzyl-4-methylphenol for thiophenol in EXAMPLE 60A.

EXAMPLE 71B

This example was made by substituting EXAMPLE 71A for EXAMPLE 1E in EXAMPLE 1F. $^1$H NMR (300 MHz, DMSO-$d_6$) δ 8.14 (d, 1H), 8.05 (d, 1H), 7.85 (m, 4H), 7.62 (m, 2H), 7.35 (m, 3H), 7.19 (m, 8H), 6.93 (d, 1H), 3.25 (s, 2H), 2.29 (s, 3H).

EXAMPLE 72A

This example was made by substituting 2-tert-butylphenol for thiophenol in EXAMPLE 60A.

EXAMPLE 72B

This example was made by substituting EXAMPLE 72A for EXAMPLE 1E in EXAMPLE 1F. $^1$H NMR (300 MHz, DMSO-$d_6$) δ 8.15 (d, 1H), 7.85 (d, 1H), 7.80 (m, 2H), 7.60 (m, 2H), 7.45 (d, 2H), 7.29 (m, 4H), 7.19 (m, 2H), 7.01 (d, 1H), 6.92 (d, 1H), 1.38 (s, 9H).

EXAMPLE 73A

This example was made by substituting 2-trifluoromethylphenol for thiophenol in EXAMPLE 60A.

EXAMPLE 73B

This example was made by substituting EXAMPLE 73A for EXAMPLE 1E in EXAMPLE 1F. $^1$H NMR (300 MHz, CD$_3$OD) δ 8.22 (d, 1H), 8.06 (d, 1H), 8.00 (d, 1H), 7.90 (dd, 1H), 7.83 (dd, 1H), 7.78 (m, 3H), 7.64 (m, 2H), 7.34 (dd, 1H), 7.23 (m, 2H), 7.12 (d, 1H), 7.06 (d, 1H), 6.88 (m, 1H).

EXAMPLE 74A

This example was made by substituting 1-adamantylmethylamine for cyclohexylpropylamine in EXAMPLE 56B.

EXAMPLE 74B

This example was made by substituting EXAMPLE 74A for EXAMPLE 1E in EXAMPLE 1F. $^1$H NMR (300 MHz, DMSO-$d_6$) δ 8.39 (t, 1H), 8.24 (s, 1H), 8.06 (s, 1H), 7.88 (m, 4H), 7.80 (d, 1H), 7.63 (d, 1H), 7.34 (m, 3H), 7.27 (d, 1H), 3.16 (d, 2H), 1.99 (s, 3H), 1.67 (d, 6H), 1.60 (s, 6H).

EXAMPLE 75A

3-Cyclohexyl-1-propylamine (200 mg), 3-phenylpropanal (150 mg), and sodium cyanoborohydride (140 mg) in THF (5 mL) at ambient temperature were stirred for 24 hours and chromatographed on silica gel with 50% ethyl acetate/hexanes.

EXAMPLE 75B

This example was made by substituting EXAMPLE 75A for cyclohexylpropylamine in EXAMPLE 56B.

EXAMPLE 75C

This example was made by substituting EXAMPLE 75B for EXAMPLE 1E in EXAMPLE 1F. $^1$H NMR (300 MHz, CD₃OD) δ 8.00 (d, 1H), 7.95 (s, 1H), 7.84 (dd, 1H), 7.74 (m, 4H), 7.53 (dd, 1H), 7.28 (m, 3H), 7.20 (m, 5H), 3.05 (m, 4H), 2.68 (t, 2H), 1.96 (m, 4H), 1.69 (m, 4H), 1.52 (m, 1H), 1.22 (m, 6H), 0.89 (m, 2H).

EXAMPLE 76A

EXAMPLE 56A (40 mg), 1,2,3,4-tetrahydro-1-naphthol (30 mg), and 60% oily NaH (8 mg) in dioxane (2 mL) at 80° C. were stirred for 24 hours, cooled and chromatographed on silica gel with 10% ethyl acetate/hexanes.

EXAMPLE 76B

This example was made by substituting EXAMPLE 76A for EXAMPLE 1E in EXAMPLE 1F. ¹H NMR (300 MHz, DMSO-d₆) δ 8.05 (m, 2H), 7.94 (m, 2H), 7.88 (m, 2H), 7.70 (dd, 2H), 7.36 (m, 5H), 7.20 (m, 3H), 5.79 (t, 1H), 2.74 (m, 2H), 2.00 (m, 2H), 1.90 (m, 1H), 1.80 (m, 1H).

EXAMPLE 77A

This example was made by substituting EXAMPLE 76A for 1,2,3,4-tetrahydro-1-naphthol in EXAMPLE 1F.

EXAMPLE 77B

This example was made by substituting 4-cyclohexyl-1-butanol for EXAMPLE 1E in EXAMPLE 1F. ¹H NMR (300 MHz, DMSO-d₆) δ 8.06 (s, 1H), 8.05 (s, 1H), 7.95 (d, 1H), 7.91 (d, 1H), 7.85 (m, 3H), 7.68 (dd, 1H), 7.38 (dd, 1H), 7.35 (m, 3H), 4.19 (t, 2H), 1.67 (m, 7H), 1.42 (m, 2H), 1.21 (m, 6H), 0.85 (m, 2H).

EXAMPLE 78A

This example was made by substituting 4-phenyl-1-butanol for 1,2,3,4-tetrahydro-1-naphthol in EXAMPLE 1F.

EXAMPLE 78B

This example was made by substituting EXAMPLE 78A for EXAMPLE 1E in EXAMPLE 1F. ¹H NMR (300 MHz, DMSO-d₆) δ 8.05 (s, 1H), 8.04 (s, 1H), 7.93 (d, 2H), 7.85 (m, 3H), 7.68 (d, 1H), 7.35 (m, 6H), 7.22 (m, 3H), 4.22 (t, 2H), 2.65 (t, 2H), 1.75 (m, 4H).

EXAMPLE 79A

This example was made by substituting cyclohexanol for 1,2,3,4-tetrahydro-1-naphthol in EXAMPLE 1F.

EXAMPLE 79B

This example was made by substituting EXAMPLE 79A for EXAMPLE 1E in EXAMPLE 1F. ¹H NMR (300 MHz, CD₃OD) δ 8.03 (s, 2H), 7.88 (m, 5H), 7.64 (d, 1H), 7.44 (d, 1H), 7.35 (m, 3H), 4.68 (m, 1H), 1.91 (m, 2H), 1.66 (m, 2H), 1.55 (m, 2H), 1.38 (m, 2H), 1.23 (m, 2H).

The foregoing is meant to illustrate the invention but not to limit it. Variations and changes obvious to one skilled in the art are intended to be within the scope of the invention as defined in the claims.

We claim:
1. A compound having formula (I),

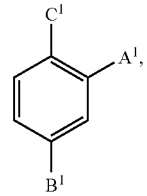

or a therapeutically acceptable salt thereof, wherein
$A^1$ is $A^2$;
$A^2$ is $C_1$-$C_5$-alkyl, $C_2$-$C_5$-alkenyl or $C_2$-$C_5$-alkynyl, each of which is substituted with $R^1$;
$R^1$ is $R^2$ or $R^3$;
$R^2$ is phenyl which is unfused or fused with benzene, heteroarene or cycloalkane;
$R^3$ is heteroaryl which is unfused or fused with benzene;
$B^1$ is phenyl substituted with one F; and
$C^1$ is C(O)OH;
wherein $R^2$ and $R^3$ are independently unsubstituted or substituted with one or two or three or four or five of independently selected $R^{17}$, $OR^{17}$, $SR^{17}$, $S(O)R^{17}$, $SO_2R^{17}$, $C(O)R^{17}$, $CO(O)R^{17}$, $OC(O)R^{17}$, $OC(O)OR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $C(O)NHOH$, $C(O)NHOR^{17}$, $C(O)NHSO_2R^{17}$, $C(O)NR^{17}$, $NHSO_2R^{17}$, $N(SO_2R^{17})_2$, $SO_2NH_2$, $SO_2NHR^{17}$, $SO_2N(R^{17})_2$, $C(O)H$, $C(O)OH$, $C(N)NH_2$, $C(N)NHR^{17}$, $C(N)N(R^{17})_2$, $N=NR^{17}$, CNOH, CNOCH₃, OH, (O), $N_3$, $NO_2$, $CF_3$, $CF_2CF_3$, $CF_2Cl$, $SO_2CF_3$, $SO_2CF_2CF_3$, $SO_2CF_2Cl$, $NHSO_2CF_3$, $NHSO_2CF_2CF_3$, $OCF_3$, $OCF_2CF_3$, F, Cl, Br or I, wherein
$R^{17}$ is $R^{18}$, $R^{20}$, $R^{20}$ or $R^{21}$;
$R^{18}$ is phenyl which is unfused or fused with benzene, heteroarene or $R^{18A}$, wherein $R^{18A}$ is cycloalkane, cycloalkene, heterocycloalkane or heterocycloalkene;
$R^{19}$ is heteroaryl which is unfused or fused with benzene, heteroarene or $R^{19A}$, wherein $R^{19A}$ is cycloalkane, cycloalkene, heterocycloalkane or heterocycloalkene;
$R^{20}$ is cycloalkyl, cycloalkenyl, heterocycloalkyl or heterocycloalkenyl, each of which is unfused or fused with benzene, heteroarene or $R^{20A}$ wherein $R^{20A}$ is cycloalkane, cycloalkene, heterocycloalkane or heterocycloalkene;
$R^{21}$ is alkyl, alkenyl or alkynyl, each of which is unsubstituted or substituted with one or two of independently selected alkyl, alkenyl, alkynyl, $R^{22}$, $OR^{22}$, $NHR^{22}$, $SR^{22}$, $S(O)R^{22}$ or $SO_2R^{22}$; and
$R^{22}$ is phenyl, heteroaryl, cycloalkyl, cycloalkenyl, heterocycloalkyl or heterocycloalkenyl, each of which is unfused or fused with, benzene, heteroarene or $R^{22A}$, wherein $R^{22A}$ is cycloalkane, cycloalkene, heterocycloalkane or heterocycloalkene;
wherein the cyclic moieties represented by $R^{18}$, $R^{18A}$, $R^{19}$, $R^{19A}$, $R^{20}$, $R^{20A}$, $R^{22}$ and $R^{22A}$ are independently unsubstituted or substituted with one or two or three or four or five of independently selected $R^{23}$, $OR^{23}$, $NHR^{23}$, $N(R^{23})_2$, $SR^{23}$, $S(O)R^{23}$ or $SO_2R^{23}$, $CF_3$, $CF_2CF_3$, OH, $NH_2$, $NHCH_3$, $N(CH_3)_2$, $N_3$, $NO_2$, $CF_3$, $CF_2CF_3$, $NHSO_2CF_3$, $NHSO_2CF_2CF_3$, $OCF_3$, $OCF_2CF_3$, F, Cl, Br or I; wherein R²³ is phenyl, heteroaryl, cycloalkyl, cycloalkenyl, heterocycloalkyl, heterocycloalkenyl or R²⁴; and R²⁴ is alkyl, alkenyl or alkynyl, each of which is unsubstituted or substituted with phenyl, heteroaryl, cycloalkyl, cycloalkenyl, heterocycloalkyl or heterocycloalkenyl.

2. A composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T cell or B cell origin, melanoma, myelogenous leukemia, myeloma, oral cancer, ovarian cancer, non small cell lung cancer, prostate cancer, small cell lung cancer and spleen cancer, said composition comprising an excipient and a therapeutically effective amount of a compound of claim 1.

3. A method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T cell or B cell origin, melanoma, myelogenous leukemia, myeloma, oral cancer, ovarian cancer, non small cell lung cancer, prostate cancer, small cell lung cancer and spleen cancer in a patient, said method comprising administering to the patient a therapeutically effective amount of a compound of claim 1.

\* \* \* \* \*

UNITED STATES PATENT AND TRADEMARK OFFICE
CERTIFICATE OF CORRECTION

| | | |
|---|---|---|
| PATENT NO. | : 7,750,004 B2 | Page 1 of 1 |
| APPLICATION NO. | : 11/482458 | |
| DATED | : July 6, 2010 | |
| INVENTOR(S) | : Wendt et al. | |

It is certified that error appears in the above-identified patent and that said Letters Patent is hereby corrected as shown below:

Column 48, line 38, claim 1: "$R^{20}$, $R^{20}$" to read as --$R^{19}$, $R^{20}$--

Column 49, line 13, claim 2: "non small" to read as --non-small--

Column 50, line 9, claim 3: "non small" to read as --non-small--

Signed and Sealed this
Twenty-second Day of February, 2011

David J. Kappos
*Director of the United States Patent and Trademark Office*